US008888718B2

(12) United States Patent  (10) Patent No.: US 8,888,718 B2
Siston et al.  (45) Date of Patent: Nov. 18, 2014

(54) JOINT STABILITY ARRANGEMENT AND METHOD

(75) Inventors: Robert A. Siston, Dublin, OH (US); Thomas L. Maack, Cincinnati, OH (US); Cornel C. Van Gorp, Powell, OH (US); Horst E. Maack, Cincinnati, OH (US)

(73) Assignee: The Ohio State University, Columbus, OH (US)

( * ) Notice: Subject to any disclaimer, the term of this patent is extended or adjusted under 35 U.S.C. 154(b) by 113 days.

(21) Appl. No.: 13/183,055

(22) Filed: Jul. 14, 2011

(65) Prior Publication Data

US 2012/0085353 A1  Apr. 12, 2012

Related U.S. Application Data

(63) Continuation of application No. PCT/US2010/021032, filed on Jan. 14, 2010.

(60) Provisional application No. 61/144,599, filed on Jan. 14, 2009.

(51) Int. Cl.
*A61B 5/103* (2006.01)
*A63B 23/08* (2006.01)
*A61B 19/00* (2006.01)
*A61B 5/00* (2006.01)

(52) U.S. Cl.
CPC .............. *A61B 19/46* (2013.01); *A61B 5/6826* (2013.01); *A61B 5/4528* (2013.01); *A61B 5/6831* (2013.01); *A61B 19/56* (2013.01); *A61B 2019/461* (2013.01); *A61B 2019/464* (2013.01); *A61B 2019/5255* (2013.01)
USPC ......................................... 600/587; 600/595

(58) Field of Classification Search
USPC ................................................. 600/587, 595
See application file for complete search history.

(56) References Cited

U.S. PATENT DOCUMENTS

| T100,602 | I4 | * | 5/1981 | Roley et al. | 600/595 |
|---|---|---|---|---|---|
| 4,583,555 | A | * | 4/1986 | Malcom et al. | 600/595 |
| 4,733,859 | A | * | 3/1988 | Kock et al. | 482/79 |
| 4,804,000 | A | * | 2/1989 | Lamb et al. | 600/587 |
| 4,825,852 | A | * | 5/1989 | Genovese et al. | 601/34 |
| 4,969,471 | A | | 11/1990 | Daniel et al. | |
| 5,014,719 | A | * | 5/1991 | McLeod | 600/587 |
| 5,211,161 | A | * | 5/1993 | Stef | 601/5 |
| 5,267,949 | A | | 12/1993 | De La Torre et al. | |
| 5,335,674 | A | * | 8/1994 | Siegler | 600/595 |
| 5,645,079 | A | * | 7/1997 | Zahiri et al. | 5/610 |
| 5,935,086 | A | * | 8/1999 | Beacon et al. | 600/595 |

(Continued)

*Primary Examiner* — Sean Dougherty
(74) *Attorney, Agent, or Firm* — Standley Law Group LLP

(57) ABSTRACT

The stability of an animal joint, especially a knee, is assessed with an arrangement having track arranged about perpendicular to the axis of the distal portion; a cart slidably engaged to the track; a fork positioned on the cart; a support adapted to receive the distal linear portion, the support connected to the fork; a lever arm connected to the support, the lever arm positioned to rotate the support about the axis of the distal portion; and at least one instrumented handle, the instrumented handle detachably engages at least one of the cart and the lever arm. In some embodiments, the fork can rotate freely on the cart. Additionally, in various embodiments, the cart may be selectively locked at a position along the length of the track. In various embodiments, the arrangement further comprises: a bracket rigidly attached to the distal portion and positioned between the support and the joint; and the at least one instrumented handle detachably engages the bracket.

18 Claims, 18 Drawing Sheets

(56) References Cited

U.S. PATENT DOCUMENTS

| | | | |
|---|---|---|---|
| 6,821,231 B1* | 11/2004 | Hall | 482/51 |
| 7,278,954 B2* | 10/2007 | Kawai et al. | 482/1 |
| 7,665,167 B2* | 2/2010 | Branch et al. | 5/624 |
| 7,753,862 B2 | 7/2010 | Branch et al. | |
| 7,878,993 B2* | 2/2011 | Agrawal et al. | 601/27 |
| 8,108,190 B2* | 1/2012 | Riener et al. | 703/11 |
| 2004/0260208 A1* | 12/2004 | Laprade et al. | 600/595 |
| 2005/0124919 A1* | 6/2005 | Castillo et al. | 600/587 |
| 2006/0019800 A1 | 1/2006 | Berger et al. | |
| 2006/0142657 A1* | 6/2006 | Quaid et al. | 600/424 |
| 2007/0054777 A1* | 3/2007 | Kawai et al. | 482/1 |
| 2007/0055176 A1* | 3/2007 | Branch et al. | 600/587 |
| 2008/0009771 A1* | 1/2008 | Perry et al. | 600/587 |
| 2008/0208081 A1* | 8/2008 | Murphy et al. | 600/595 |
| 2009/0124936 A1* | 5/2009 | Branch et al. | 600/587 |
| 2010/0010397 A1* | 1/2010 | Ochi et al. | 601/27 |
| 2010/0145233 A1* | 6/2010 | Zhang et al. | 600/592 |
| 2012/0046540 A1* | 2/2012 | Branch et al. | 600/415 |
| 2013/0041289 A1* | 2/2013 | Sena et al. | 600/595 |

\* cited by examiner

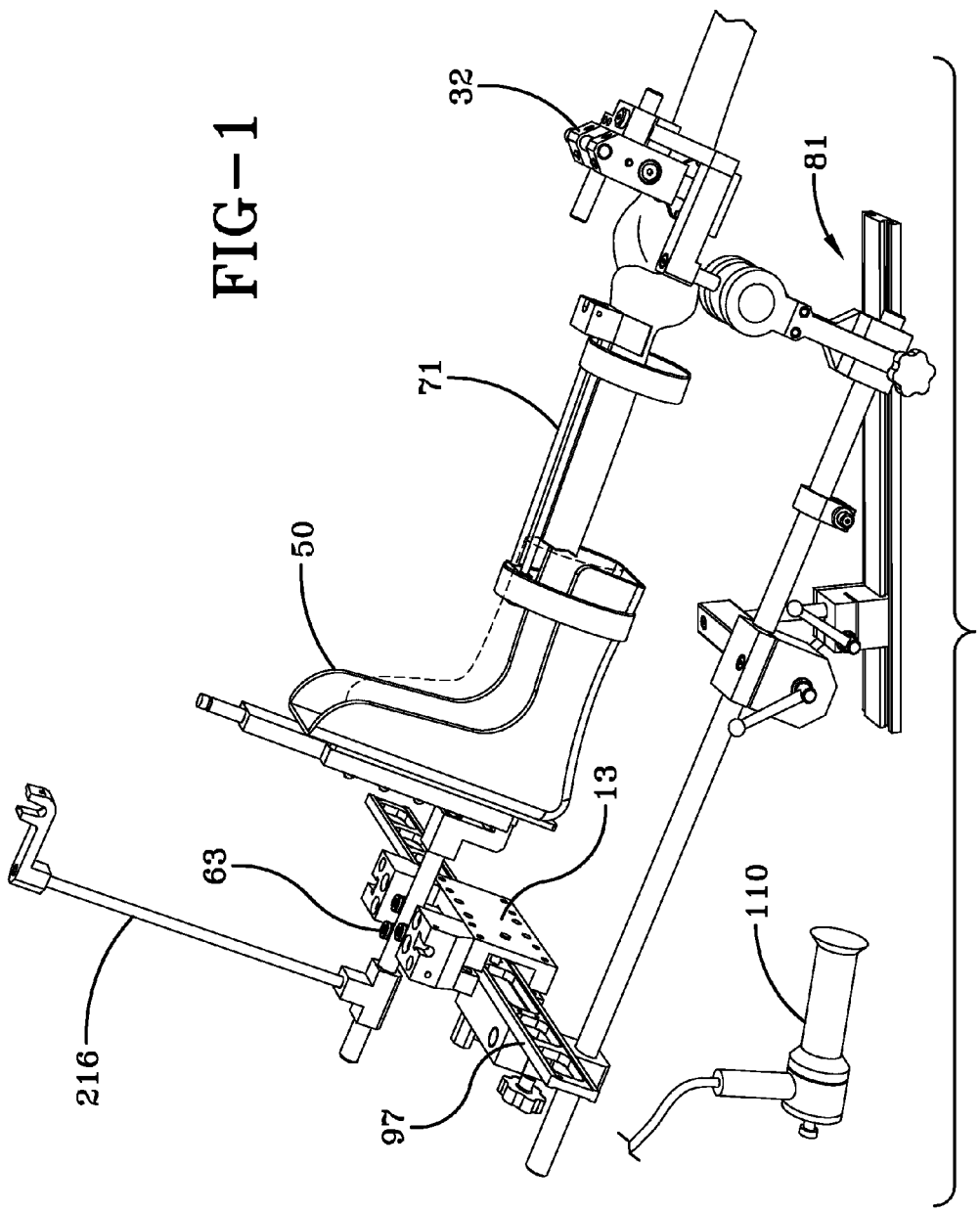

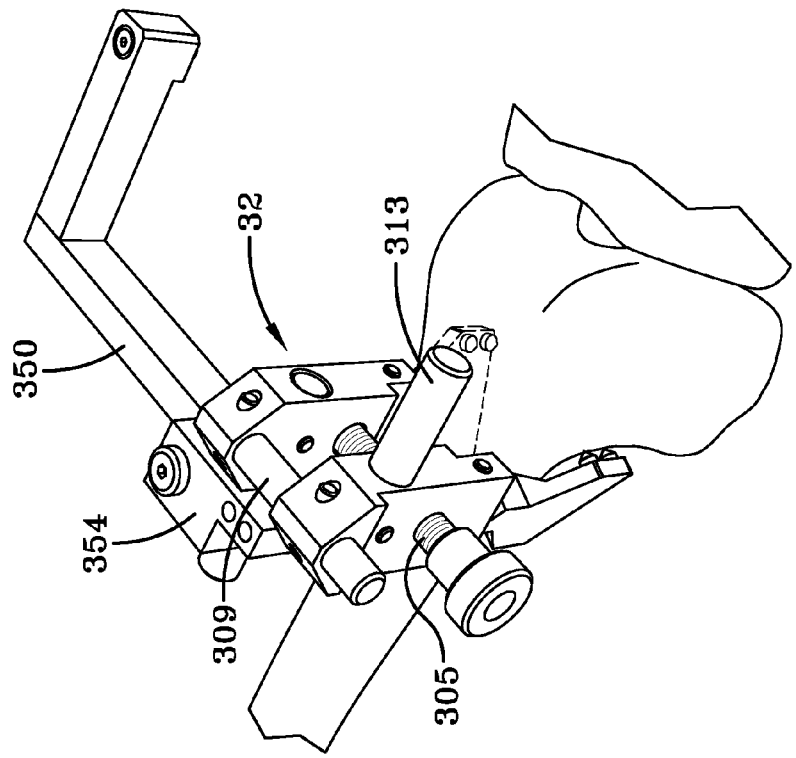
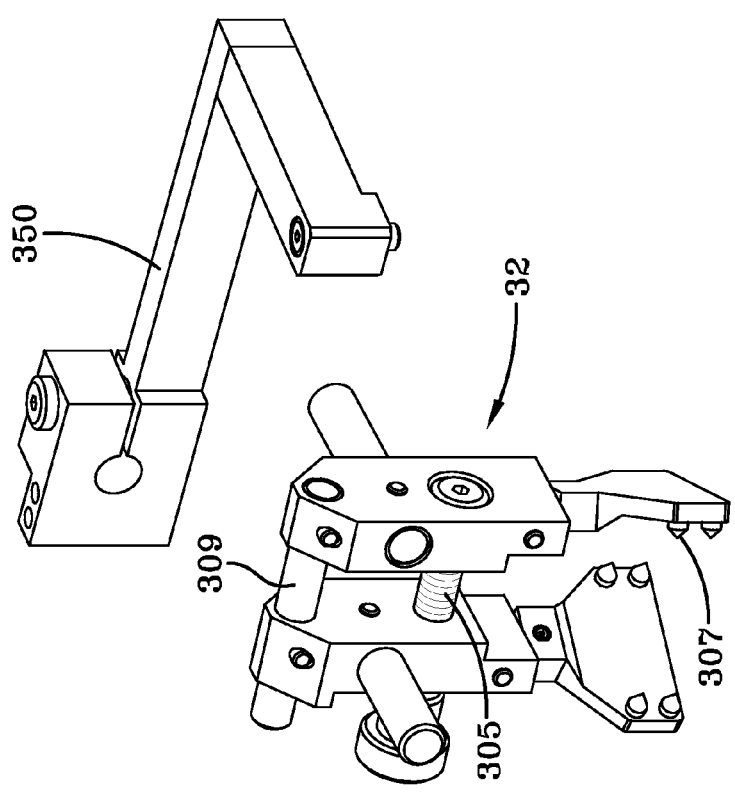

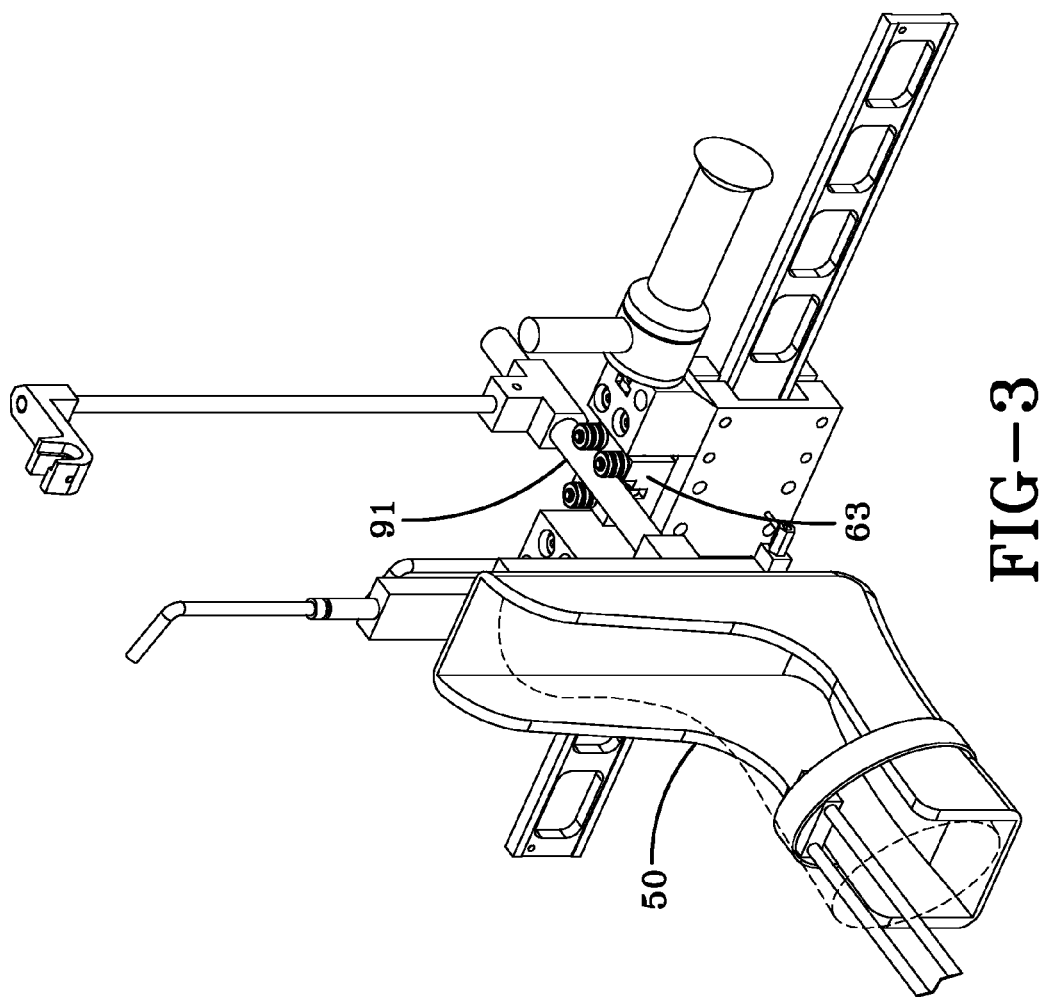

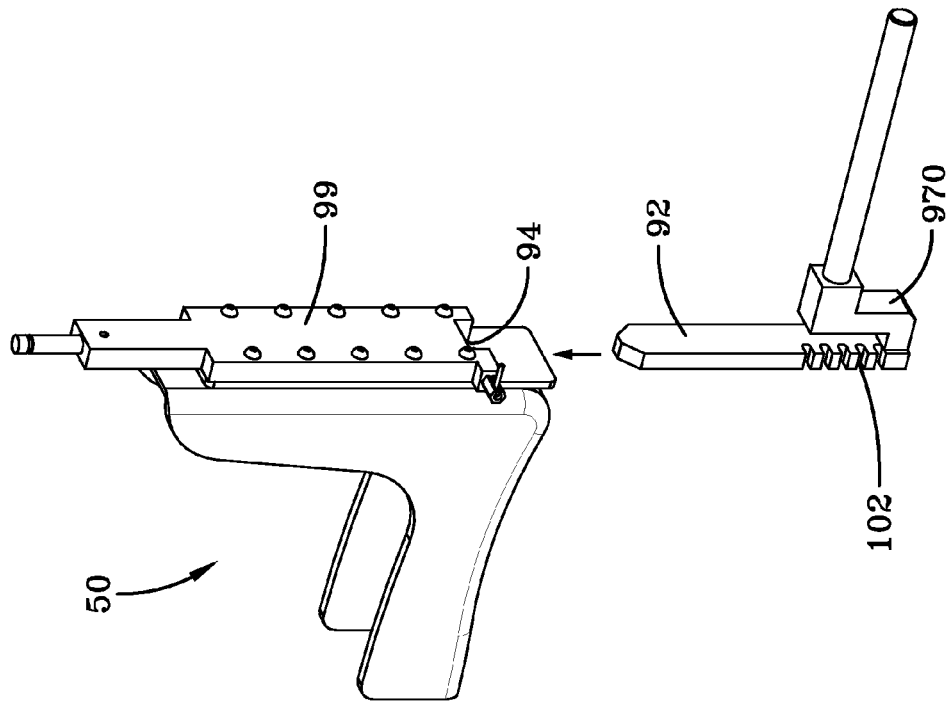
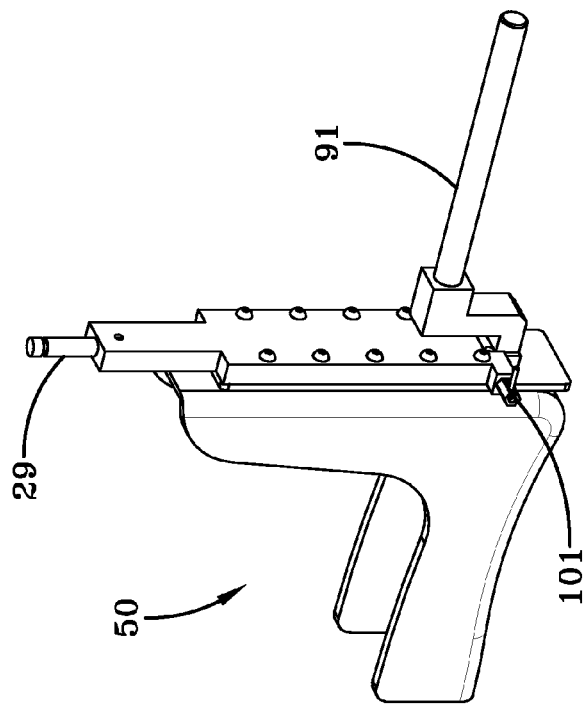
FIG-4B
FIG-4A

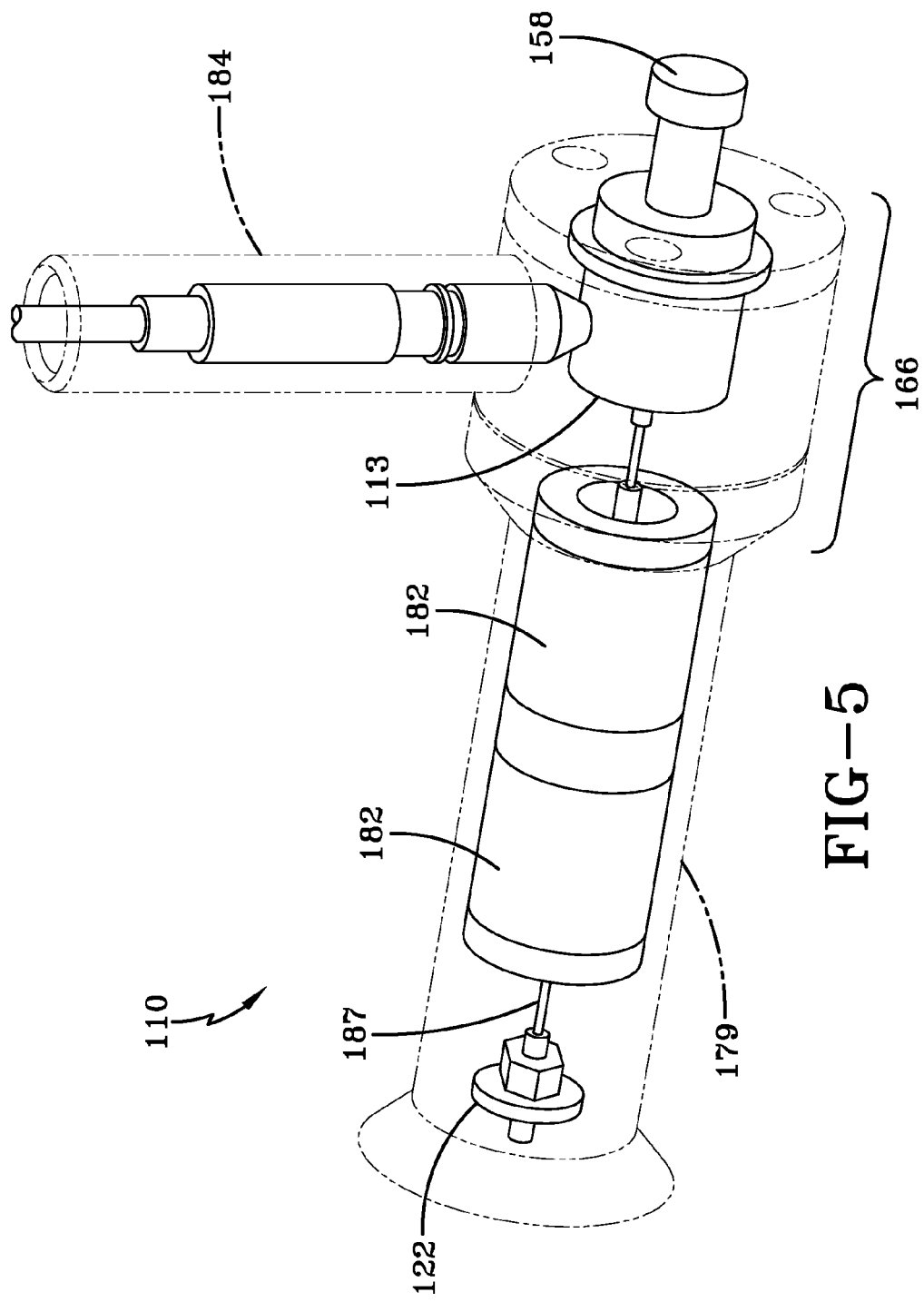

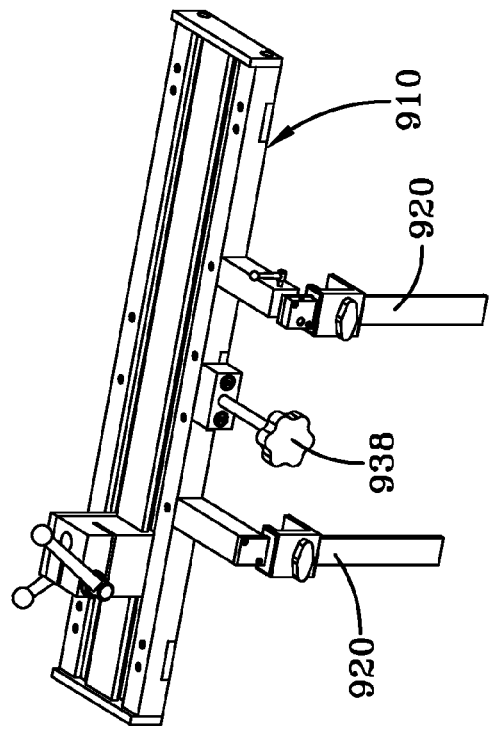
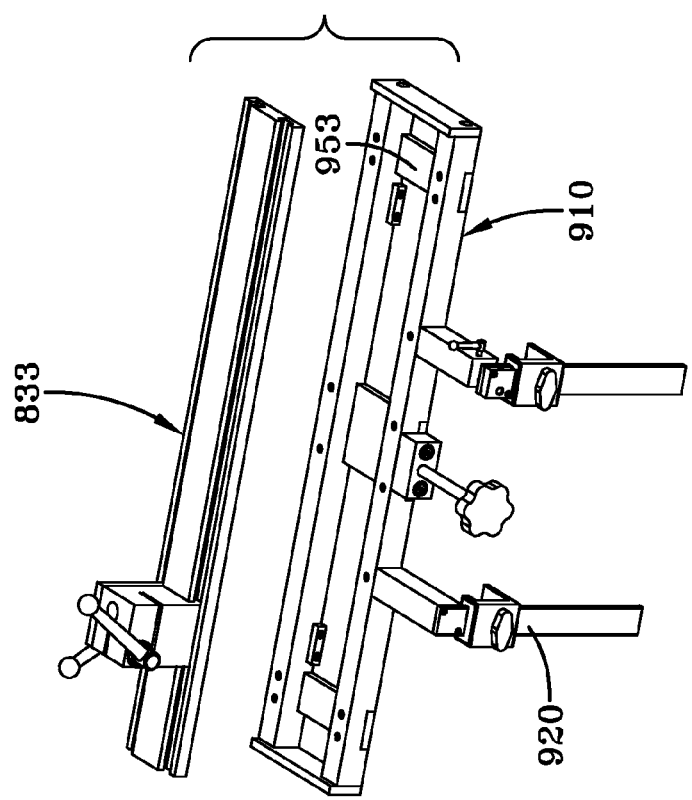
FIG-13B
FIG-13A

JOINT STABILITY ARRANGEMENT AND METHOD

CROSS-REFERENCE TO RELATED APPLICATIONS

This non-provisional patent application claims the benefit of priority from PCT/US2010/021032, filed 14 Jan. 2010, which is in turn entitled to the benefit of priority from U.S. Provisional Patent Application No. 61/144,599, filed Jan. 14, 2009, which is hereby incorporated by reference in its entirety.

TECHNICAL FIELD

The disclosed embodiments relate generally to the field of medicine. More specifically, embodiments relate to arrangements and methods for assessing joint stability of an animal.

BACKGROUND OF THE ART

The success of a total knee arthroplasty (TKA) may be determined, in part, by the ability of a surgeon to adequately manage (or balance) the soft tissues surrounding the joint. Postoperative malalignment or imbalance of the collateral ligaments can lead to a lax joint and result in early loosening and instability, and leaving the knee too tight may cause stiffness and limited motion. The severity and location of wear patterns on the polyethylene insert are also associated with knee stability from ligament balancing. Establishing a balanced soft tissue envelope remains a challenge that may be not always achieved, and instability, tightness, and wear that result from unbalanced knees may necessitate revision surgery or result in reduced patient satisfaction.

Despite the importance of joint stability to the success of the operation, debate exists regarding how much soft tissue balancing may be appropriate. In general, surgeons believe that the knee should not be too tight and that a little varus-valgus laxity should be achieved postoperatively, with the ideal knee being looser in flexion than in extension, and looser laterally (i.e., under varus stress) than medially, but little evidence supports these beliefs. No available data quantifies a "loose" or "tight" knee. While many surgeons have become skilled in developing a qualitative "feel" for knee laxity or stiffness, an objective definition as to what constitutes acceptable post-operative stability does not exist, and establishing an objective definition for knee stability may be an important step toward improving surgical reconstructions.

Having the ability to accurately and precisely measure intra-operative joint stability represents a key requirement in the process of objectively defining acceptable joint stability and would mark a substantial improvement over the subjective measurements currently made by surgeons.

SUMMARY

This and other unmet needs of the prior art are met by the apparatus and method as described in more detail below. Embodiments include an arrangement for assessing stability of a joint between a proximal linear portion and a distal linear portion of an animal, comprising: a track arranged about perpendicular to the axis of the distal portion; a cart slidably engaged to the track; a fork positioned on the cart; a support adapted to receive the distal linear portion, the support connected to the fork; a lever arm connected to the support, the lever arm positioned to rotate the support about the axis of the distal portion; and at least one instrumented handle, the instrumented handle detachably engages at least one of the cart and the lever arm. In some embodiments, the fork can rotate freely on the cart. Additionally, in various embodiments, the cart may be selectively locked at a position along the length of the track.

In various embodiments, the arrangement further comprises: a bracket rigidly attached to the distal portion and positioned between the support and the joint; and the at least one instrumented handle detachably engages the bracket.

In some embodiments, the at least one instrumented handle comprises a tension/compression load cell. In various embodiments, the at least one instrumented handle detachably engages the cart and the lever arm in one of two oppositely disposed orientations. In exemplary embodiments, the at least one instrumented handle further comprises linear bearings and a semi-flexible rod.

In various embodiments, the arrangement may further comprise a clamp positioned for rigid attachment to the proximal portion, the clamp is adapted to hold the proximal portion stationary during the stability assessment. Arrangement may comprise a frame for rigidly connecting the track and the clamp, the frame may adjust to maintain a flexion angle between the proximal linear portion and the distal linear portion of 0 to about 90 degrees. In exemplary embodiments, the frame comprises a telescoping rod. The frame of an exemplary embodiment may further comprise a ball clamp that connects the track and the clamp.

An exemplary embodiment may comprise a system for tracking the position and orientation of the distal portion relative to the proximal portion as the joint is manipulated to determine its three-axis stability. In some embodiments, this will be a navigation system that comprises optical trackers, a camera, and a computer. The computer may be programmed to receive information regarding the position and orientation of the distal portion, the proximal portion, the support, and the cart and incorporate data from the instrumented handle to calculate joint motions and applied forces/moments in real time. Various embodiments comprise a graphical user interface for displaying the joint motions and applied forces/moments. A navigation system of this type would be considered to be passive and would operate independently from the surgeon, although providing input to the surgeon. In other embodiments, the function of tracking position and orientation could be achieved by an at least semi-active system, especially a system involving robotic elements, since tracking position and orientation is inherent in operation of robotics. In such a situation, the robot could be actively operated by the surgeon or could be preset to provide feedback to the surgeon as limits or boundaries are approached.

In various embodiments, the support comprises a boot. The boot may comprise a detachable peg, the peg protrudes coaxially from the distal linear portion. In some embodiments, the anterior/posterior position of the peg relative to the distal portion is adjustable.

BRIEF DESCRIPTION OF THE DRAWINGS

A better understanding of the exemplary embodiments of the invention will be had when reference may be made to the accompanying drawings, wherein:

FIG. 1 is a perspective view of exemplary embodiment showing the femur clamp, surgical boot, instrumented handle, varus/valgus track, internal/external lever arm, and anterior/posterior bracket;

FIGS. 2A and 2B show perspective views of a femur clamp of an exemplary embodiment, with FIG. 2A showing the clamp apart from the support link and FIG. 2B shows the clamp rigidly fixed to the support link and associated with a model femur;

FIG. 3 is a perspective view of surgical boot supported in the fork using a peg at the distal end of the boot of an exemplary embodiment;

FIGS. 4A and 4B show two perspective views of an exemplary boot comprising a multiple position detachable boot peg;

FIG. 5 shows a schematic view of an instrumented handle illustrating the handle's inner construction in an exemplary embodiment;

FIGS. 13A and 13B show the pan in plate rigid table attachment of an exemplary embodiment, with FIG. 13A showing the plate apart from the pan for clarity and FIG. 13B showing the plate secured into the pan;

DETAILED DESCRIPTION

Figure 6:
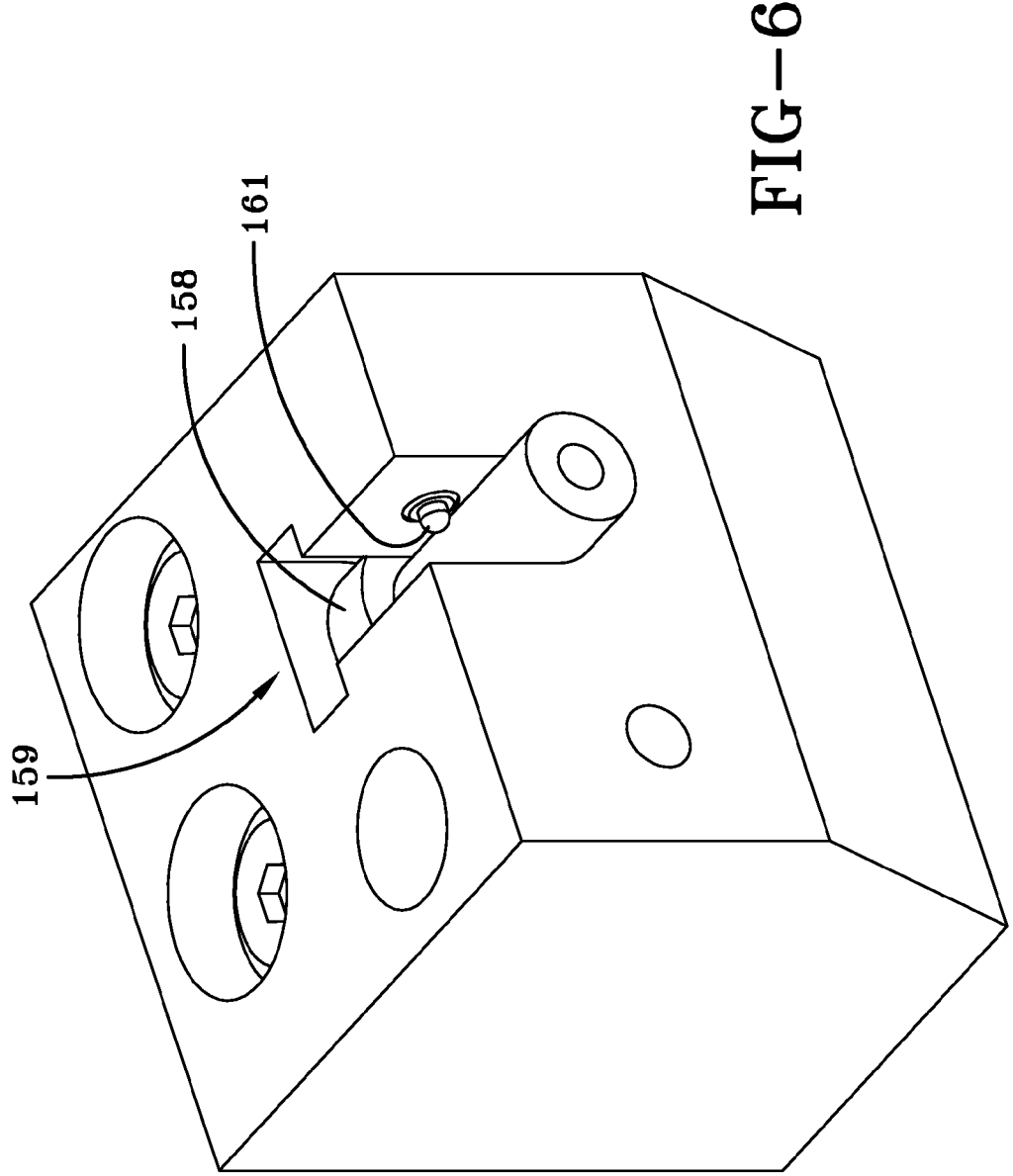
FIG. 6 shows a perspective the cylindrical head and neck member on the front end of the instrumented handle, with the head and neck member shown engaged with matched receiver slots positioned upon various components of an exemplary arrangement.

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, the phrase "operably connected" may be intended to mean coupled or connected, either directly or indirectly, such that the connected structures are operable to perform a desired function.

As used herein, the word "animal" broadly refers to any member of Kingdom Animalia, a Kingdom that includes humans, primates, and other mammals.

FIG. 1 shows an exemplary embodiment. An exemplary embodiment facilitates repeatable and accurate application of varus/valgus moment, internal/external torque, and anterior/posterior force. In an exemplary embodiment, varus/valgus, internal/external, and anterior/posterior stability measurements between about 0° and about 90° of knee flexion may be performed. An exemplary embodiment comprises several components. A femur clamp 32 can be used for rigid attachment to the distal metaphysis of femur, thereby holding the thigh stationary during stability tests, although there are several other devices known and used in the operating room to achieve this function. Flexion angle may be maintained with the help of a boot 50 which may be supported by a fork 63, allowing for some decoupled motion of the knee. All three loads are applied using an instrumented handle 110 that may comprise a tension/compression load cell (not shown). The instrumented handle 110 may be removably attached to various components of the device depending on the given measurement. Alternative embodiments may have more than one instrumented handle 110. Additionally, other types of load cells, for example, rotational load cells, may be advantages for specific applications, such as the internal external stability measurement.

In various embodiments, varus/valgus moments may be applied by pushing and pulling a cart 13 to which the fork 63 may be connected along a low friction track 97 that runs medial/lateral to the leg. Internal/external moments may be applied by attaching a lever arm 216 to the boot 50 and then applying a force to the far end of the lever arm 216. Anterior/posterior force may be applied through a bracket 71 which attaches to the leg with hook and loop fastener (e.g., VELCRO™ straps) or other suitable fastening means. In various embodiments, a navigation system may be used to track the position and orientation of the femur, tibia, boot, and/or varus/valgus cart. In preferred embodiments, the navigation system can incorporate data from the load cell to calculate and display knee motions and applied forces/moments in real time. An exemplary embodiment may further comprise a frame 81 for rigidly attaching the femur clamp 32 and the varus/valgus track 97.

FIGS. 2A and 2B show a femur clamp 32 of an exemplary embodiment. In FIG. 2A the clamp is shown apart from link 350 for clarity. The femur clamp 32 may be tightened onto the bone using a stud 305. For ease of use, the stud may be tightened from both the medial and lateral side of the clamp 32. To tighten the stud 305, an Allen wrench may be used to engage nuts affixed to either end of the stud 305. In various embodiments, the tightening motion may be guided with a clamp rod 309 that runs parallel to the stud 305 and takes bending moment off of the stud 305 by stabilizing the clamp 32. In various embodiments, the clamp rod 309 may be rigidly fixed to one side wall of the clamp 32 and slide freely through an aperture on an oppositely disposed side wall. Preferably, the sliding end of clamp rod 309 engages the side wall aperture with sufficient overlap to resist bending moment.

In an exemplary embodiment, clamp 32 grasps the femoral bone surface instead of skin, to avoid problems of relative skin to bone motion. The medial and lateral clamping surfaces may pivot relative to the top sections of the femur clamp 32 (FIG. 2A). Because the femoral shaft widens distally along the distal metaphysis, the clamping surfaces of an exemplary embodiment pivot in the femur's coronal plane on small rods (not shown) that connect the clamping surfaces to the top of the femur clamp. At least one protrusion 307 on each clamping surface may be positioned to allow for better traction of the bone surfaces.

Referring to FIG. 2B, clamp 32 may be rigidly attached to the distal metaphysis of a femur, thereby holding the thigh stationary for various stability tests. In an exemplary embodiment, the femur may be held stationary with clamp 32 even when high loads are applied to the knee, permitting smoother application of loads. As discussed in more detail below, one or more femoral optical trackers (not shown) may be used by a navigation system to determine the position and orientation of the femur. The optical tracker may be attached to the distal metaphysic (not shown). A connection member 354 on link 350 that supports the femur clamp 32 attaches to the posterior side of the clamp 32 to give clearance to a femoral tracker (not shown). When the femur clamp 32 is tightened, the rod 309 and the stud 305 project out of the clamp. To avoid femoral tracker interference with rod 309 and stud 305, the entire stud was designed to flip 180 degrees. The flip feature may be created by two transverse rods 313, which project from either the proximal or distal side of the femur clamp 32. Depending on the orientation, one of the two of these rods 313 may be rigidly engaged to the support link 350.

Referring to FIG. 3, flexion angle may be maintained with the help of a modified surgical boot 50. The surgical boot 50 may be supported using a fork 63, allowing for some decoupled freedom of motion. In various embodiments, the boot 50 may be a modified aluminum Alvarado boot (Zimmer, Warsaw, Ind.) typically used to stabilize the knee during TKA surgery through a hook connection with a plate on the operating room table. The patient's foot may be held in the boot 50 by wrapping the boot and foot in elastic medical wrap. An exemplary embodiment includes a boot peg 91 which extends out perpendicular from the sole of the boot 50. This may sit in a fork 63, maintaining flexion angle by posteriorly supporting the distal leg. The boot peg-to-fork interface allows the leg and boot to translate proximal/distally and rotate freely in all three planes of the leg, thereby allowing freedom of coupled knee motions.

Referring again to FIG. 3, the boot peg 91 of an exemplary embodiment is preferably long enough to allow the boot peg 91 to engage the fork 63 even if the leg may be at variable distances from the fork 63. In this way, the peg 91 may slide proximal/distal in the fork during the varus/valgus stability test. Additionally, during setup of the device, the relative position of the fork to the femur clamp may be adjusted for the patient's leg length.

With reference to FIGS. 4A and 4B, to allow the boot 50 to rest at the level of the operating room table, the boot peg 91 was designed to be detachable. A quick but rigid attachment may be created by operably connecting the boot peg 91 to a vertical member 92 which may then slide into a slot 94 created at the heel of the sole of the boot 50. The slot 94 on the heel of the sole of the boot may be formed by additional plates, one may be the sole of the boot 50 and the other may be a cover plate 99 with a rim on the plate's medial, lateral, and anterior sides forming the slot 94. The foot may be secured in the Alvarado boot with elastic medical wrap which may lie against the outer surfaces of the boot 50. This attachment is preferably designed to avoid interference with the sole of the boot 50 to ensure that the foot may still be tightly wrapped. In an exemplary embodiment, the slot 94 openings may be positioned at the heel of the sole of the boot to ensure that most of the sole remains unobstructed. To bridge the gap between the plate 99 which slides into the slot 94 and the boot peg 91, a neck 970 may connect to the posterior distal surface of the plate, protruding out distally, and rising anteriorly, before attaching to the boot peg 91. In various embodiments, this neck 970 may be L-shaped to create sufficient clearance between the proximal end of the boot peg 91 and the sole of boot 50 (FIG. 4A).

In an exemplary embodiment, the boot peg 91 should preferably form an extension of the leg's mechanical axis so that varus/valgus and internal/external moments are applied about their correct axes. Because different foot and leg sizes may shift the long axis of the leg anterior/posterior relative to the boot and this may decrease the accuracy of the varus/valgus and/or internal/external stability tests, embodiments may provide the plate that slides anterior into slot 94 at the heel of the boot 50, facilitating anterior/posterior adjustment of the boot peg 91.

In various embodiments, a retractable spring plunger 101 (FIG. 4A) built into the cover plate may be used to lock the anterior/posterior position of the plate which slides into the slot 94. The spring plunger may be retracted before the peg's plate slides into the slot 94 and may be then released to find engagement bores 102 in the peg's vertical member 92.

In an exemplary embodiment, a navigation system and computer programmed with software may be used to locate the correct anterior/posterior boot peg 91 location. After the vertical member 92 has been positioned and locked with the spring plunger, a reference pin may be inserted into the peg's plate to allow the operator to quickly relocate the correct anterior/posterior position of the peg for the second round of stability tests after the prosthesis may be in place.

In an exemplary embodiment, an optical tracker 29 attaches to the boot 50 through a stem that extends from the anterior portion of the slot cover plate 99 (FIG. 4A). This stem on the cover plate extends the tracker anterior to the foot. The optical tracker allows the navigation system to record position and orientation information of the boot.

Instrumented Handle

Referring to FIG. 5, in an exemplary embodiment, forces may be applied using at least one instrumented handle 110. Instrumented handle 110 comprises a load cell 113. Various embodiments may employ a commercial 1001b tension/compression load cell 113 (e.g., Sensotec, Morristown, N.J.) contained in the instrumented handle 110. In an exemplary embodiment, the load cell 113 may be a single-piece, welded, stainless steel design that allows repeated sterilization. In embodiments where the same instrumented handle 110 is used for all stability tests, the same load cell 113 measures loads for all stability tests. In various embodiments, the load cell 113 within instrumented handle 110, may be connected to a DAQ system with a quick disconnect RJ50 cable. The DAQ permits connection to a computer with a USB cable.

Small unwanted loads may contribute to a false reading or may otherwise damage a load cell. Various embodiments include features to protect the load cell 113 from unwanted loads. Various embodiments protect the load cell 113 with a handle that essentially excludes all but forces along the measurement axis of the load cell 113. Referring to FIG. 5, an exemplary load application handle 110 may comprise a set of linear bearings 182 (e.g., Part 6262K84, McMaster-Carr, Elmhurst, Ill.) in the handle to ensure that non-axial loads are absorbed by the handle and not transferred to the load cell 113. The linear bearings 182 may be composed of a stainless steel shell and stainless steel bearing balls, making them resistant to corrosion from sterilization. In various embodiments, the instrumented handle 110 may be constructed of two distinct parts, a handle member 179 which the operator grabs and an engagement member 166 with means for engaging various components of the arrangement for stability testing and houses the load cell 113. The set of linear bearings 182 may be contained inside of the handle member 179. The handle member 179 necks down to allow the linear bearings 182 and the handle member 179 to slide relative to one another. Two or more linear bearings 182 may be used for better moment support. A dowel pin with a sliding fit bridges the two sections and rotationally constrains them relative to each other. In a preferred embodiment, the handle doesn't spin when used. In various embodiments, a cylindrical head and neck member 158 projects from front end of the engagement member 166.

The load cell 113 may be attached to the front portion of the engagement member 166 of the instrumented handle 110 by a stud located on the load cell 113. A semi-flexible handle member rod 187 runs the length of the handle member 179 and attaches to the load cell 113 by way of a threaded section at one end of the rod 187. The other end of the rod 187 may also have a threaded section. A washer 122 may be held onto this section by nuts. The washer 122 in turn catches the back section of the handle member end cap (not shown), securing the rod to this section. The use of a washer 122 held in place by nuts allows for fine tuning of the relative position of the front and back sections of the instrumented handle 110. Assuming the linear bearings 182 have negligible friction, essentially all the force between the front and back sections of the handle may be transferred through the rod 187 to the load cell 113.

Shear force and moments in the rod caused by tolerances in the handle and its bearings could lead to false tension/compression force readings. Accordingly, to minimize the creation of such loads and potential resulting false readings of the load cell 113, various embodiments increase the flexibility of the rod 187 by adding additional sections. False readings of the load cell 113 may also be caused by unwanted loads that may occur if force may be applied to the cable which projects out of the handle. To minimize this source of error the cable may be shielded by a pipe 184 projecting radially out from the instrumented handle 110.

In a number of embodiments the handle 110 may engage various components of the device for the varus/valgus, internal/external, and anterior/posterior stability tests.

Referring now to FIG. 6, in various embodiments, a rigid but detachable engagement is created when the cylindrical head and neck member 158 on the front end of the instrumented handle slides into matched receiver slots 159 positioned upon various components of the device (FIG. 6). In some embodiments, a ball spring plunger 161 along these receiver slots 159 provides downward force on the handle's cylindrical neck when engaged.

In an exemplary embodiment, sterilization of the handle may be performed in a disinfecting bath. Accordingly, an exemplary embodiment may include drainage holes to allow fluid to easily flow in and out of the inside cavities of the handle.

Track

Figure 7:
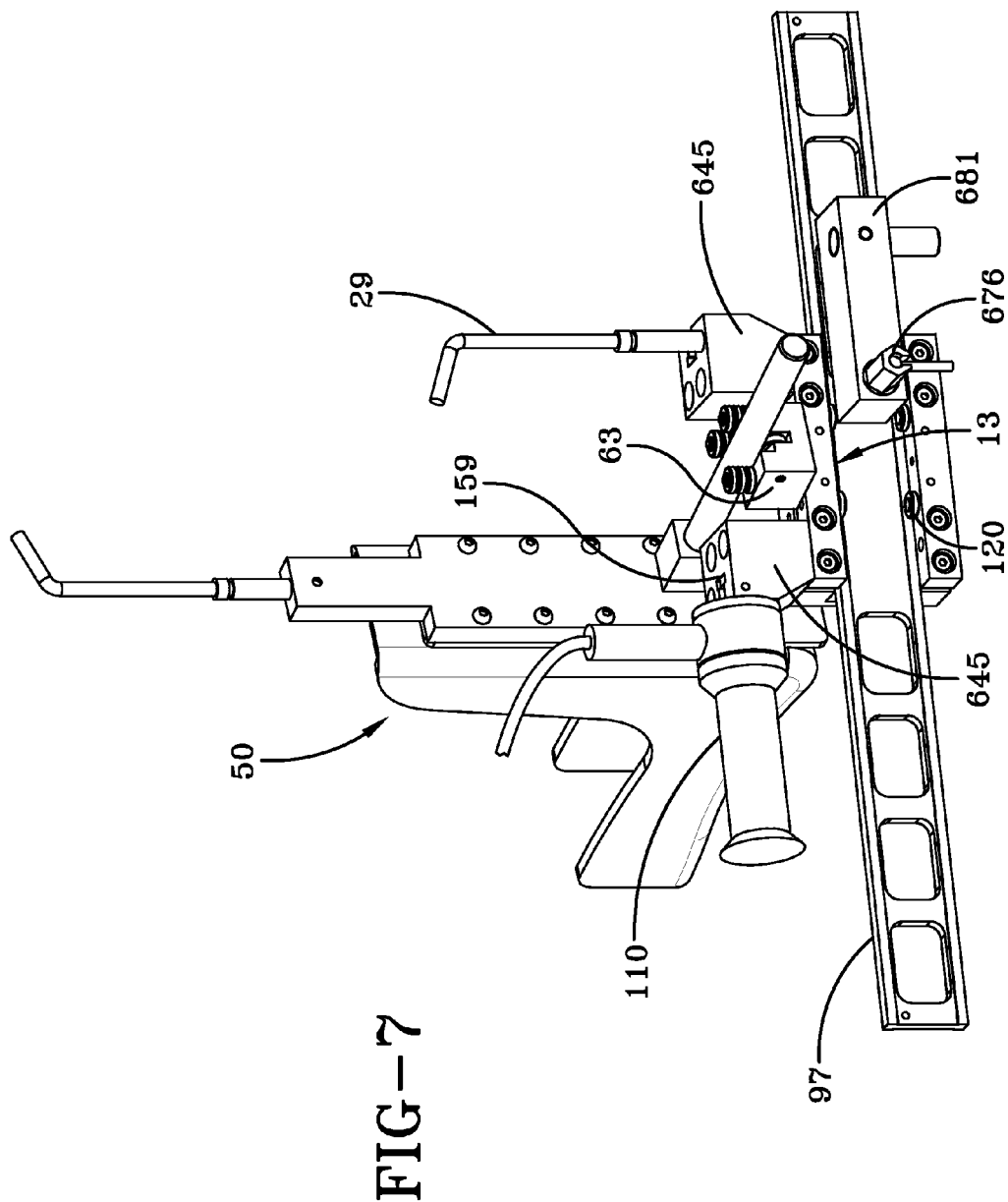
FIG. 7 shows the varus/valgus track component with the boot engaged in a fork on the cart.

FIG. 7 shows the varus/valgus low friction track 97 component with the boot 50 engaged in fork 63. The track 97 is shown disconnected from the support frame for clarity. In the current design, varus/valgus moment may be applied by pushing and pulling a cart 13 along a low friction track 97 which may run medial/lateral to the leg with instrumented handle 110 (as shown in FIG. 7). The track ensures that force is applied in a repeatable direction by constraining the handle's 110 position. Also, it ensures that unwanted loads are not transferred to the leg but are dissipated to the track rail, further increasing repeatability. High repeatability of varus/valgus stability tests is particularly important to assessing accuracy of surgical technique. A main goal may be to create a knee which is properly balanced in the coronal plane. The cart fork-to-boot peg interface allows for freedom of coupled motions of the knee.

The varus/valgus cart 13 may comprise radial ball bearings 120 to allow it to slide with negligible friction along track 97, ensuring that the only force measured by the handle 110 may be the resistive force from the leg. As shown, the rectangular track 97 may have cut out windows to decrease weight. The distal side of the track 97 may be screwed to a block 681 that connects down to the frame supporting the device. The cart 13 may be adjusted to pull the radial bearings tightly against the track 97. In exemplary embodiments, the cart may be constructed of three parts held together by screws, thereby allowing the bearings anterior and posterior to the track 97 to be adjusted such that they lie flush against the track 97. The cart may also comprise at least two slots on the upper and lower sections of the cart. These cart slots allow additional screws to narrow the slot and pull the radial bearings proximal and distal to the track 97 flush to the track 97. To prevent the cart from sliding off the end of the track 97, screws may be positioned in the track 97 and cart 13 so as serve as end stops as cart 13 traverses track 97.

Referring again to FIG. 7, for the varus/valgus stability test, blocks 645 at either end of the cart 13 have receiver slots 159 for both the instrumented handle and an attachment point for an optical tracker 29. Placing a block at either end of the cart allows the stability test to be performed from both the medial and lateral sides of the patient and ensures that the optical tracker 29 of track 97 will not be blocked by the patient's foot and boot 50. Finally, a spring plunger 676 connected to the track 97 can be released to engage the cart 13 and hold it stationary for the internal/external and anterior/posterior stability tests.

Figure 8:
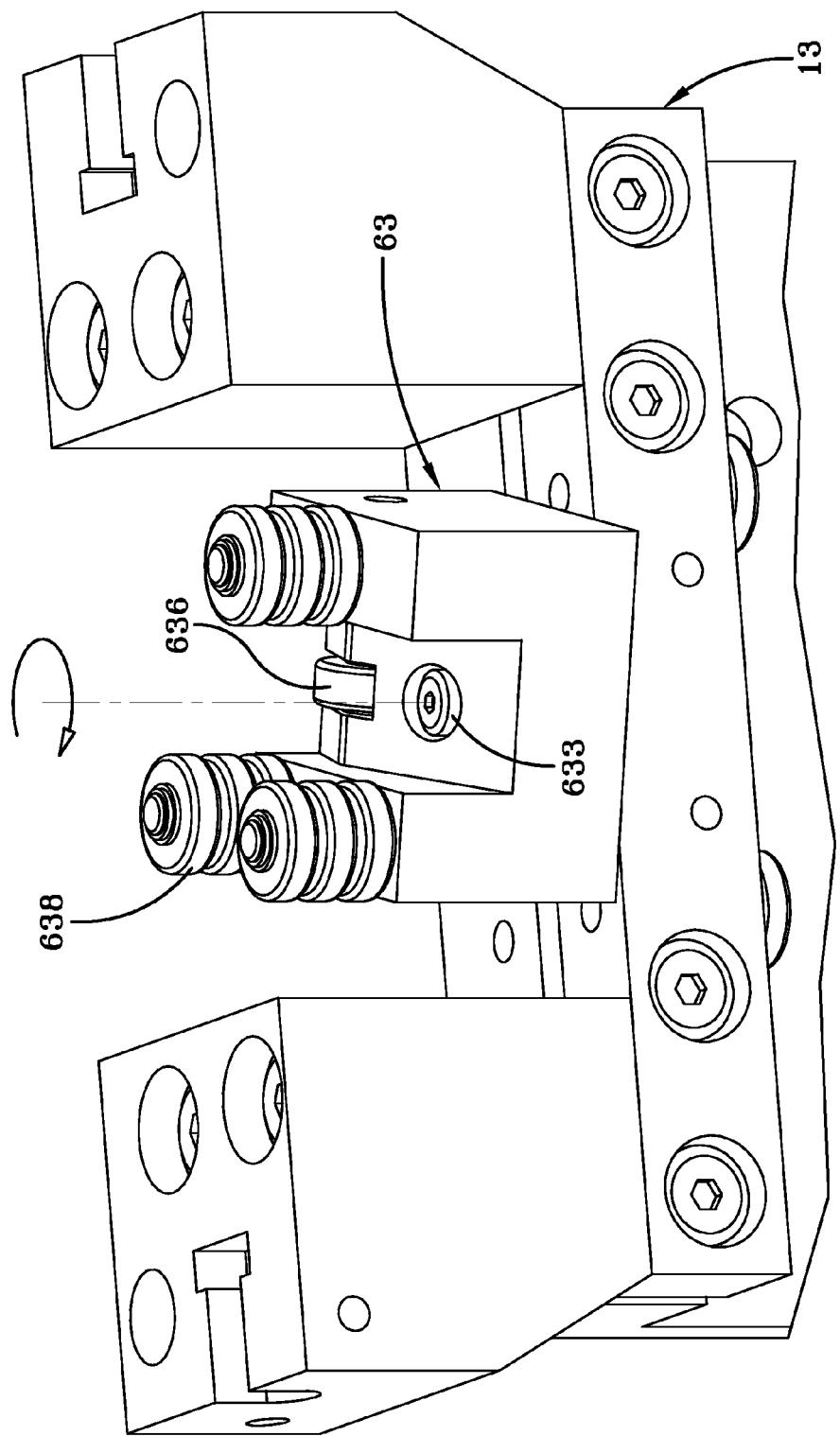
FIG. 8 shows a close up perspective view of the fork attached to the cart so the fork rotates freely about an axis.

Referring to FIG. 8, the fork 63 may attach to the cart 13 with a dowel pin 633 allowing the fork to rotate freely about an axis. The dowel pin may be rigidly attached to the fork and may be held in the cart with three radial bearings, sunk into the cart and not visible in FIG. 8. These bearings also allow for low friction rotation. The use of three bearings give the dowel pin better stability against axial force and bending moments in the bearings than if a single bearing were used.

A posterior bearing 636 in the fork 63, located posterior to the boot peg, supports the boot peg (not shown in this Figure) against posterior force and gravity, thereby maintaining flexion angle. In the example embodiment, the fork 13 comprises a stack of three radial bearings 638 on the medial and lateral sides of the fork 13 for holding the boot peg in the fork 63. In this embodiment, three bearings ensure that the boot peg (not shown) would have to visibly move anterior before it could disengage the fork 63. As illustrated in FIG. 8, various embodiments keep the fork 63 and boot peg aligned in the coronal plane by positioning two stacks of radial bearings 638 on the right side of the fork 63, thereby creating a two point contact on the boot peg. The posterior bearing 636 and the stacked medial and lateral bearings 638 are the only locations of contact with the boot peg.

Internal/External Lever Arm

Figure 9:
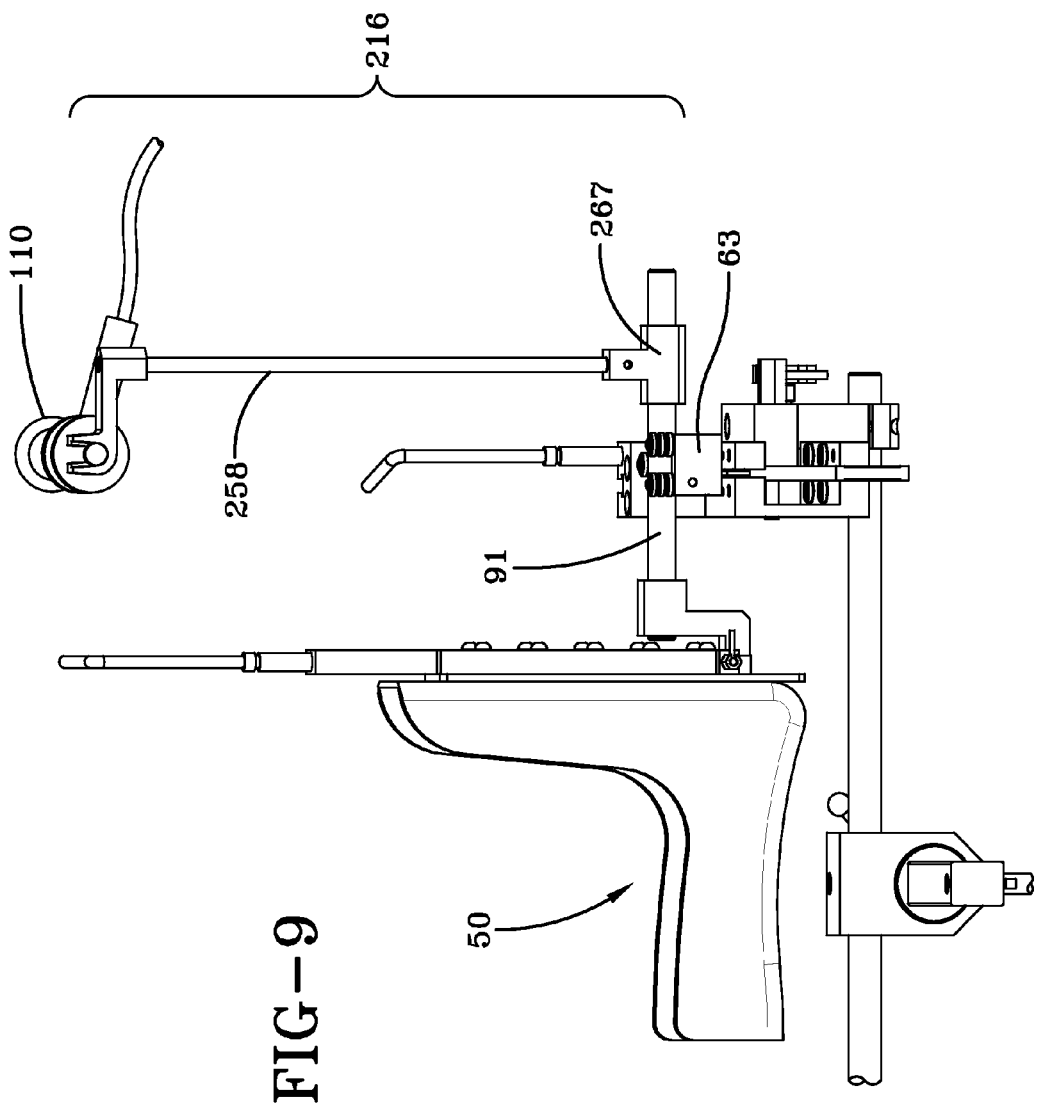
FIG. 9 shows a lever arm connected to the boot via the boot peg of an exemplary embodiment.

Referring to FIG. 9, internal/external torque may be applied by attaching a lever arm 216 of a predetermined length to the boot peg 91 and then applying a force to the far end of the lever arm 216. One end of the lever arm 216 slides onto and off of the boot peg 91 and allows for quick attachment and detachment of the lever arm 216. Rotation between the lever arm 216 and the boot peg 91 at this connection location may be constrained by a rectangular channel running along the anterior surface of the boot peg 91 which may be engaged by a rectangular key on the lever arm 216 (not shown). In an exemplary embodiment, the length of the lever arm 216 may comprise a rod 258 which keeps weight down over the use of one continuous piece of rectangular stock. The rod connects to a fitting member 267 on one end of the lever arm 216 which may slide onto the boot peg 91 from the location of force application.

For the internal/external stability test, the instrumented handle 110 engages the far end of the lever arm 216. Receiver slots allow the instrumented handle 110 to connect to both the medial and lateral sides of the lever arm 216, allowing the stability test to be performed from both sides of the patient. When force is applied to the handle, the fork which supports the boot peg 91 applies a resistive force. This resultant force couple produces a torque about the boot peg 91. Assuming the boot 50 is aligned on the leg, this torque about the boot peg 91 may be analogous to an internal/external torque.

If the handle 110 is located anywhere but directly anterior to the fork, a resultant varus/valgus moment is created. To avoid a varus/valgus moment, the lever arm 216 was designed to extend the location of force application out towards the fork 63. When the lever arm 216 may be slid onto the boot peg 91, it may be positioned by the operator such that the location of force application may be visibly anterior to the center of the fork 63, negating any varus/valgus moment creating lever arm 216 (FIG. 9). Finally, to reduce the ratio of unwanted loads to desired internal/external torque, a relatively long lever arm 216 may be used so that any force applied along the desired axis of force application results in a relatively large torque about the boot peg 91. In an alternative embodiment, the use of a cuff about the boot peg 91 may be used to constrain the axis of torque application. This sort of cuff would ensure that unwanted loads of distal/proximal force and non-internal/external moment cannot be applied to the leg using the lever arm 216.

In an exemplary embodiment, the lever arm 216 may be attached to the boot peg 91 quickly, reducing setup time. Some coupled motions of the knee can be allowed if they are not constrained by the operator. This design may be relatively simple and works well with the design of the fork.

Anterior/Posterior Bracket

Figure 10:
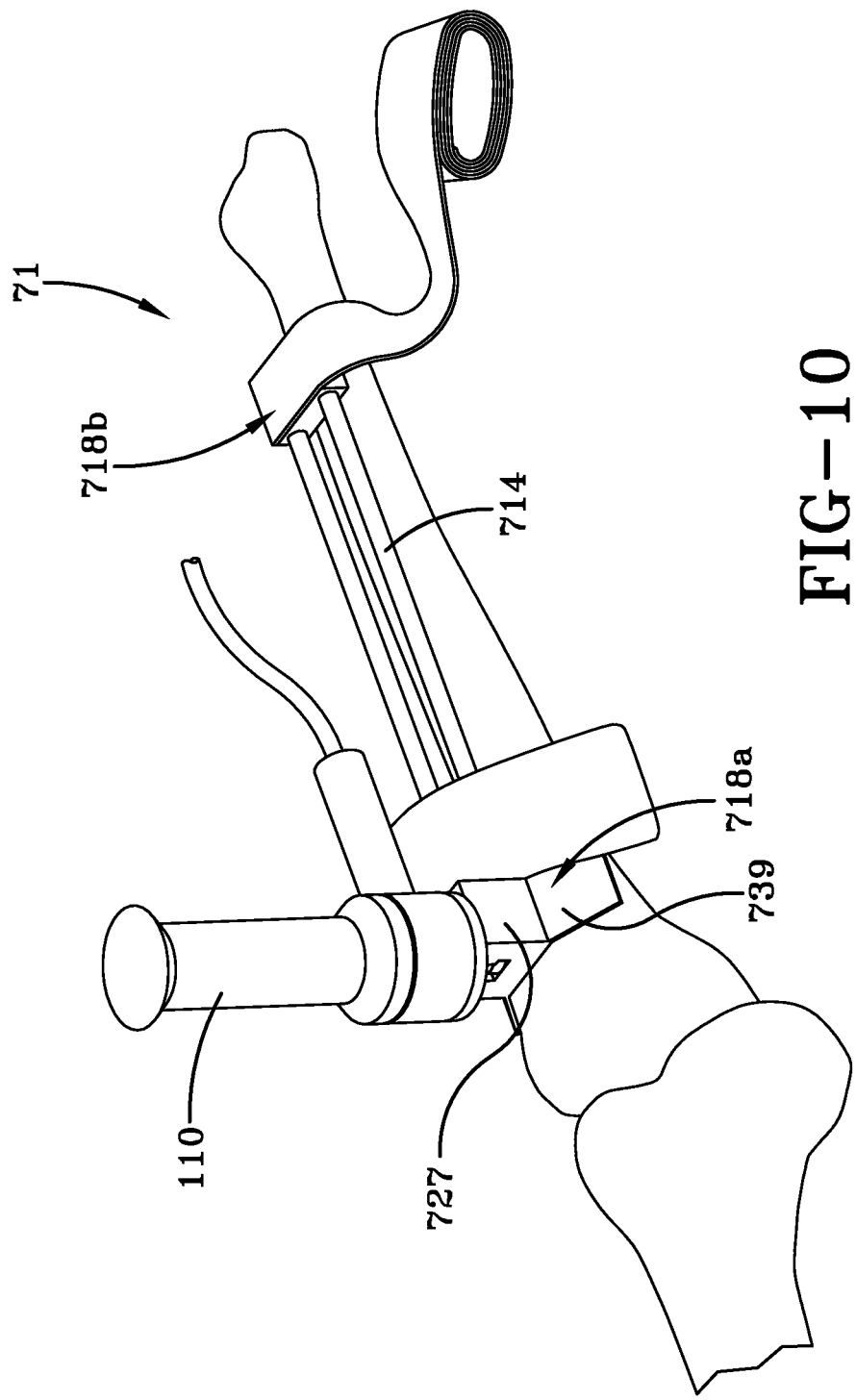
FIG. 10 shows a perspective view of an instrumented handle attached to the anterior/posterior stability test bracket, the bracket is shown fixed on a model limb.

Referring to FIG. 10, the anterior/posterior stability test bracket 71 may be placed on the leg directly distal to the incision. The bracket 71 attaches on the anterior side of the leg and rests against the leg using two pads, located at the proximal and distal end of the bracket 71. The proximal pad 718*a*, placed just distal to the incision of the knee, may be V-shaped and matches the anterior crest of the tibia. The distal pad 718*b* may be flat, allowing it to rest well against the distal leg.

In an exemplary embodiment, both pads (718 *a, b*) are constructed of a rectangular piece of stock 727 with sheet metal plates 739 welded on the posterior surface. The sheet metal plates protrude out from the rectangular stock and give increased surface area to the pads without unnecessarily increasing weight. The rectangular stock pieces 727 provide the necessary thickness for a slot engagement for the instrumented handle 110 and attachment of the rods 714 which connect the pads 718 a, b together. The rods 714 are spaced to give the bracket stability while the use of rods 714 minimizes weight. Hook and loop fasteners (e.g., Velcro™ strips, Part 96125K61, McMaster-Carr, Elmhurst, Ill.) attach to the proximal and distal pads to hold the bracket 71 to the leg.

Referring again to FIG. 10, anterior/posterior force may be applied through the instrumented handle 110 to the proximal pad 718*a* of the bracket 71. Because forces are transferred directly to the bracket, unwanted loads applied by the operator to the handle are transferred to the leg. Alternative embodiments may include a constraint, such as a cuff, to allow for exclusively anterior/posterior motion of the handle 110.

In an exemplary embodiment, anterior/posterior displacement in the current design may be measured directly using sensors attached to the femur and tibia instead of measuring the position of the patella to represent the femur. Also, if the arrangement is used during surgery, the patient is sedated so as to prevent error to do to the application of muscle forces across the knee joint which could change stability with the degree of muscle excitation.

Adjustable Support Frame

Figure 11:
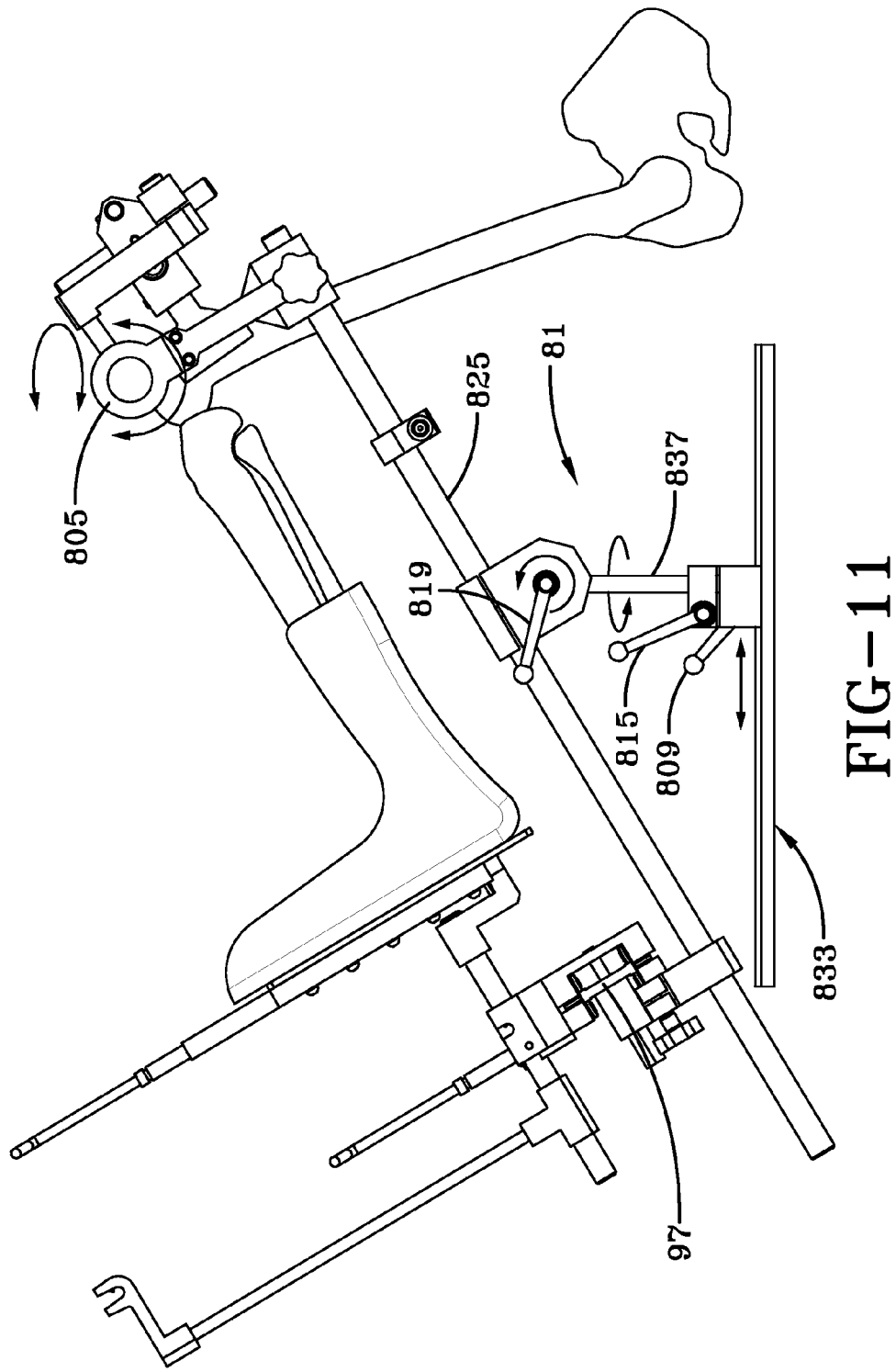
FIG. 11 shows a side view of an adjustable frame from an exemplary embodiment.

Referring to FIG. 11, an exemplary embodiment comprises a frame for rigidly attaching the femur clamp (not shown) and the varus/valgus track 97 to the operating room table, while four adjustable clamps in the frame allow for adjustment between different flexion angles without requiring the position of the patient to be changed. Rigid fixation of the femur clamp and varus/valgus track 97 may be important for several reasons. Motions of the thigh and track 97 could undermine stability data depending on the rate at which the navigation system tracks position and orientation data. Furthermore, once the clamps are positioned the stability analysis may be run relatively quickly without having to worry about constraining the thigh and holding the varus/valgus track 97. Finally, in the current design only four clamps are needed to adjust the frame between different flexion angles, making adjustment of the frame relatively simple. In various embodiments, extra rigidity in the frame may be added by linking the femur clamp and the varus/valgus track 97 with a long telescoping rod 825 running parallel to the leg which may be interrupted by one clamp for flexion angle adjustment, the ball clamp 805. The ball clamp 805 may be free to rotate in three planes.

Referring again to FIG. 11, an exemplary embodiment may comprise a base frame 81 with four clamps. The four clamps of the frame may be the ball clamp 805, which lies medial/lateral to the knee, the proximal/distal linear clamp 809, the turning clamp 815, and the tilt clamp 819 (FIG. 11). The ball clamp 805 between the rod running parallel to the leg and the femur clamp allows for varying of flexion angles within the frame. The tilt clamp 819 was designed with a wedge shape that creates a mechanical advantage for the clamp. The turning clamp 815 holds a frame rod 837 from the upper part of the frame into a sliding fit bore on the lower frame. A slot allows the two sides of the bore to pivot and be pulled together by the stud. The proximal/distal linear clamp 809, which allows translation of the upper part of the frame along the plate 833, is integrated into a cart that slides along a rail on the plate 833. The base frame cart is constructed of two sides which are pulled together by stud and pivot at their anterior ends, thereby pulling them against the rail.

In various embodiments, a ball clamp 805 may be preferable to a rotary clamp because the knee does not move as a perfect hinge. Also the femur clamp may not be perfectly aligned with the axes of the femur. To minimize relative translation between the rod and the leg, the ball clamp 805 may be placed along the axis of knee flexion. This may be accomplished by placing the ball clamp 805 directly medial or lateral from the epicondyles of the femur, as the transepicondylar axis has been reported to be a good approximation of the axis of rotation of the knee.

Figure 12:
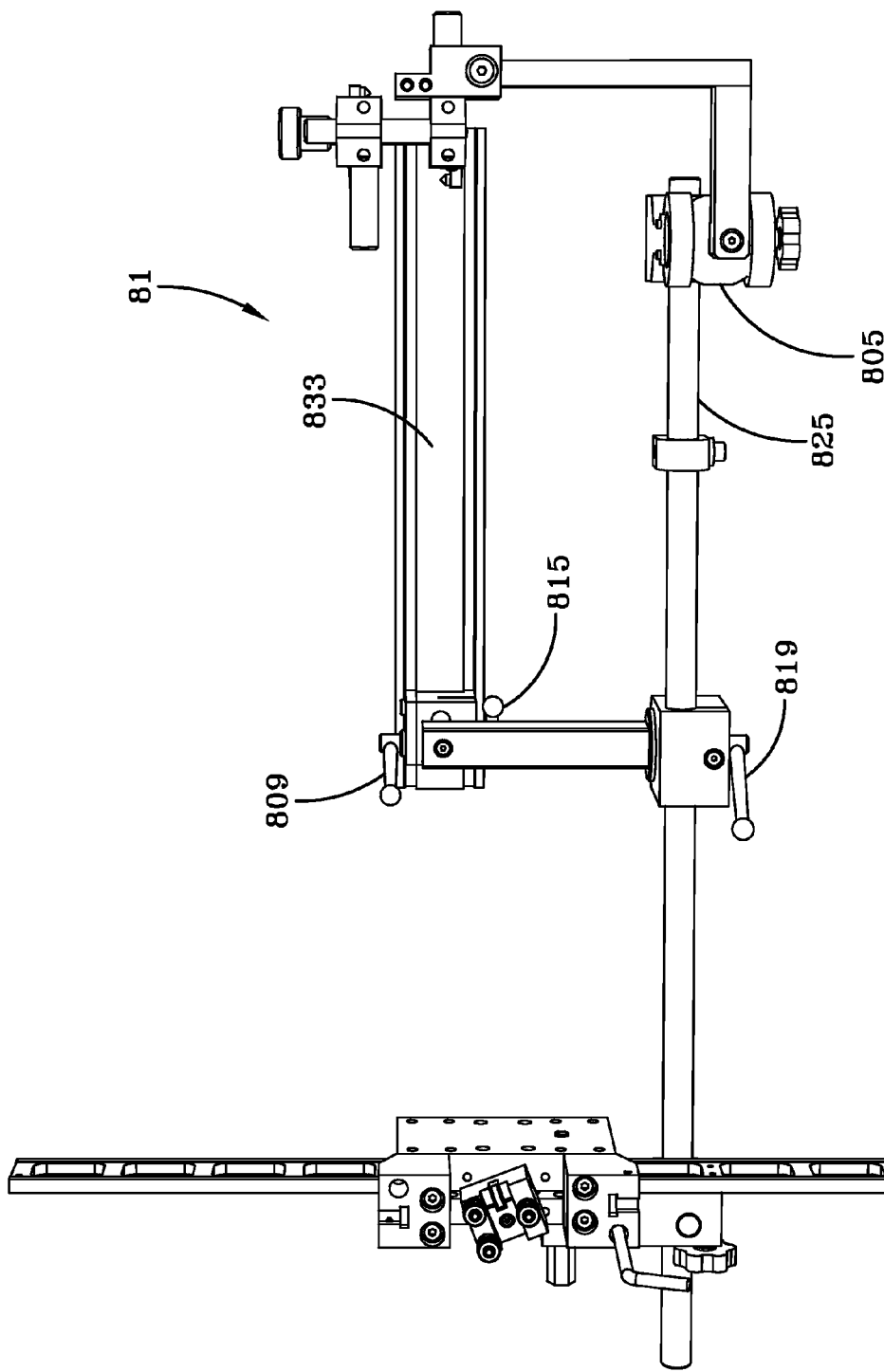
FIG. 12 shows a top elevation view of an adjustable frame from an exemplary embodiment.

In an exemplary embodiment, and with reference to FIG. 12, a plate 833 on the table forms the base of the frame 81 and operably connects to the telescoping rod 825 running parallel to the leg with the remaining three clamps. From the plate 833 to the rod 825, a proximal/distal clamp 809 allows proximal/distal translation of the upper part of the frame along the plate 833. The second clamp, or turning clamp 815, enables rotation in the plane of the table's surface. These first two clamps, proximal/distal translation clamp 809 and turning clamp 815, allow the upper part of the frame to adjust to the location and orientation of the patient on the table. Accordingly, moving the patient to accommodate the stability test may be unnecessary. The third clamp, or tilt clamp 819, provides rotation in the sagittal plane, thereby allowing the upper part of the frame to adjust to the angle of the leg.

These four clamps allow for relatively simple adjustment but are still able to provide adjustment for all possible patient locations. These four clamps may be tightened and loosened using built in knobs and handles so no extra tools are necessarily required in this embodiment. The four clamp system offers many advantages. Even so, alternative embodiments with fewer or more clamps are also possible depending on the application.

In an exemplary embodiment, the frame 81 may be designed to allow for adjustability from 0 to at least about 90 degrees of knee flexion and for patients of almost any height. Additionally the frame was designed to allow the sole of the foot to fork distance to be varied. This range gives the frame extra flexibility for accurate setup. To accommodate ranges for leg length and sole of foot to fork distance, the rod running parallel to the leg can also be telescoped between lengths.

The frame may also maintain sufficient clearance with the operating room table for the above mentioned flexion angles and patient heights. In an exemplary embodiment, at least two parameters may varied to ensure clearance: the height of the tilt clamp above the plate and the distance of the tilt clamp to the distal end of the rod running parallel to the leg.

The ball clamp 805 (FIG. 12) may be rotated so that the knee may be in full extension and at least about 105 degrees of flexion, allowing the ball clamp to adjust for misalignment of the femur in the femur clamp. The ball clamp also allows for about 20 degrees of rotation in the non-sagittal planes, again allowing the ball clamp to compensate for misalignment of the femur in the femur clamp. The two sides of the clamp may have 50 degree angled surface which allow the ball to lay tangent to these surfaces and create circles of contact with the ball. The two sides of the clamp pivot towards and away from the ball on a set of screws. The heads of these screws sit on spherical washers which allow misalignment. A stud with a knob, opposite the ball, pushes the two sides of the clamp apart. The combination of the stud and the pivot causes a clamping force along the circular contacts of the ball to resists pivoting.

Referring to FIG. 13, a pan 910 secures the plate 833 through the sterile drapes. In FIG. 13, the pan is shown above the sterile drapes for clarity, (left) pan and plate separate; (right) plate engaged in pan. The plate 833 on the table may be clamped into a pan 910 which may be located below the sterile drapes and rigidly clamped to the table. Thereby, the frame may be securely fastened to the table. The pan 910 clamps to the table rail and utilizes the table surface for a broad base. The pan-plate interface provides rigidity while not tearing the sterile drapes. In an exemplary embodiment, the pan has two legs 920 which hang over the edge of the table and are clamped to the table's rail with standard rail clamp. The plate 833 may be rigidly fixed in the pan with a clamp on the pan 910. The plate 833 may be clamped into the pan 910 with a stud located on the pan by rotating the stud's knob 938 to tighten. In exemplary embodiments, the pan clamp may feature a 15 degree dove tail to push the plate down into the pan when clamped. The plate 833 may be supported from below with struts 953 running across the base of the pan 910.

When the surgery and stability tests are finished, the entire arrangement may be disassembled into manageable parts for sterilization and transport. The varus/valgus track disconnects from the frame by loosening a knob. The top of the frame can be disconnected from the base of the frame as may be done in when the leg positioner and the top of the frame are exchanged. The rod running parallel to the leg can either be telescoped to a shorter length or disassembled into two rods. The plate of the base of the frame detaches from the pan.

In an exemplary embodiment, stainless steel may be used for components close to the knee such as the femur clamp, ball clamp, and anterior/posterior bracket and components that needed extra strength such as the rod running parallel to the leg, turning clamp, proximal/distal linear clamp, and varus/valgus rail. Aluminum may be used for the remaining components to keep weight down. Sterilization using an autoclave oven may be the most widely used form of sterilization in hospitals. All components are designed to be sterilized in an autoclave except the instrumented handle which may be sterilized in a disinfecting bath.

Navigation System

Figure 14B:
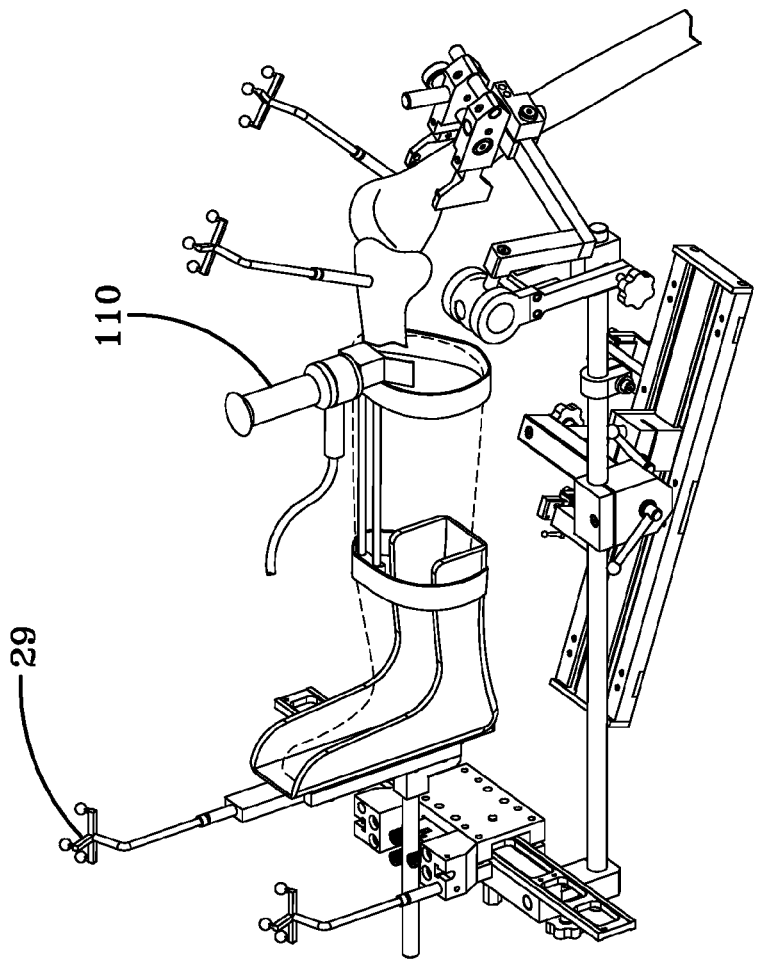
FIGS. 14A and 14B show a navigation system from an exemplary embodiment, with FIG. 14A showing the camera and computer and FIG. 14B showing the optical trackers arranged at various points on the components.
Figure 14A:
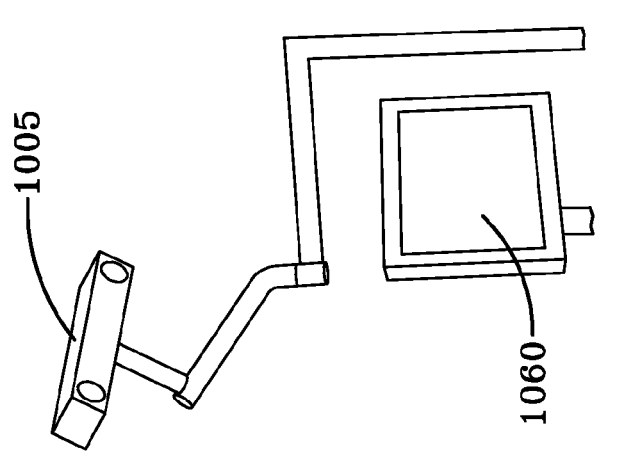

Referring to FIGS. 14A and 14B, an exemplary embodiment comprises a navigation system that may include various components including optical trackers 29, a camera 1005, a signal conditioning unit, and a computer 1060. In exemplary embodiments, the custom surgical navigation system may be used to track the position and orientation of the femur, tibia, boot and varus/valgus cart, and incorporate data from the load cell in the instrumented handle 110 to calculate and display knee motions and applied forces/moments in real time. As shown in FIG. 14, optical trackers 29 are rigidly attached to each of these objects at appropriate locations. Rigid attachment of the optical trackers to the objects is created by connecting the tracker to a stem which in turn engages a base fixture rigidly attached to the object. Exemplary embodiments may employ wireless passive optical trackers, (e.g., Traxtal Inc., Toronto, Ontario, Canada), that may possess one or more reflective spheres. These spheres are tracked by a camera 1005 (e.g., Polaris hybrid position sensor, NDI, Waterloo, Ontario, Canada) with a linear accuracy of 2 mm and angular accuracy of at least about 1.25 degrees. A signal processor (not shown), (e.g., Polaris enhanced tool interface unit, NDI, Waterloo, Ontario, Canada) may connect the camera 1005 and computer 1060. In alternative embodiments, other types of navigations systems may be used. For example, electromagnetic tracking systems may be used in various embodiments.

Figure 15:
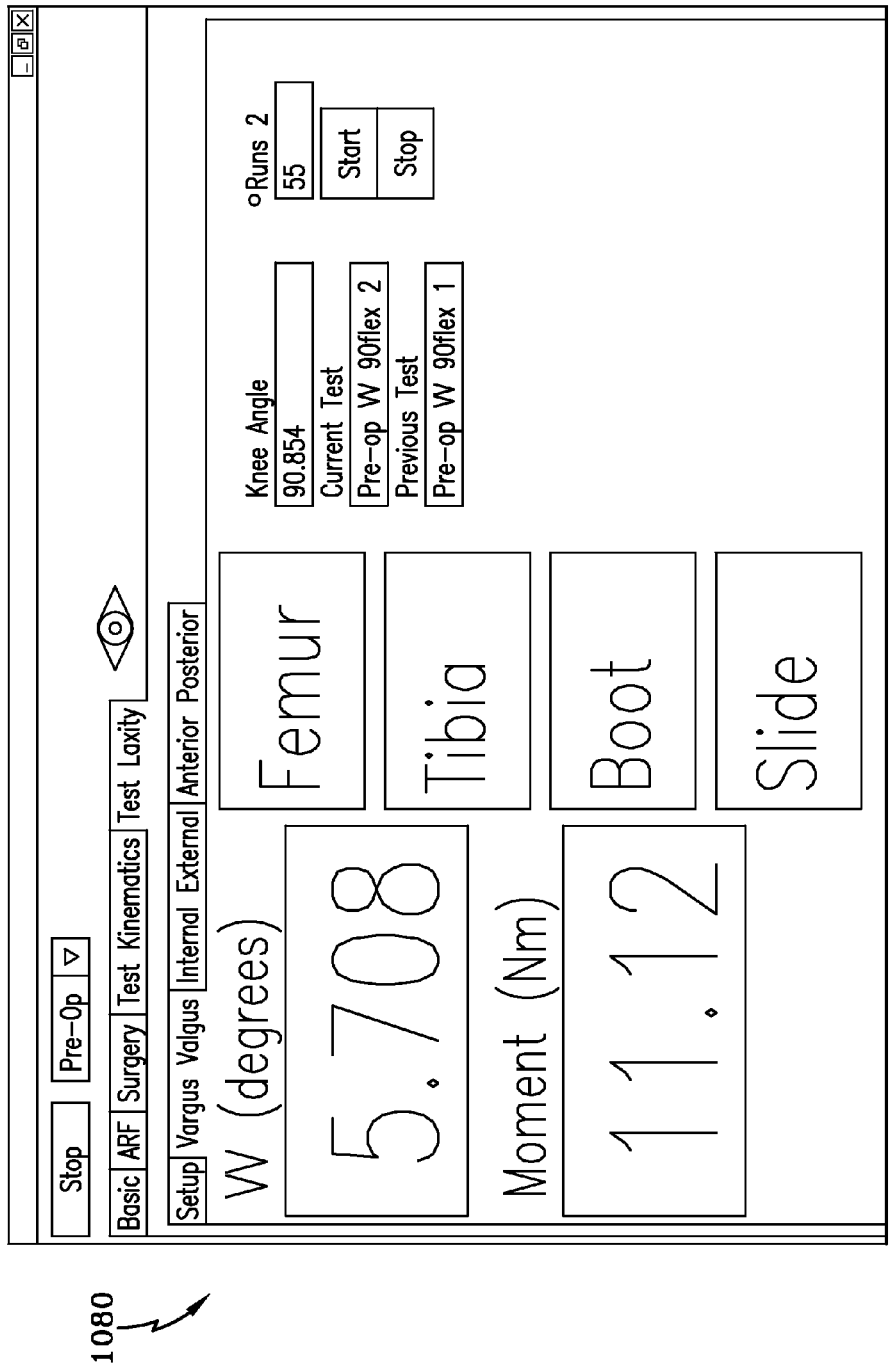
FIG. 15 shows an exemplary screen shot from a graphical user interface of an exemplary embodiment.

Referring to FIG. 15, a graphical user interface 1080 displays information relating to the navigation system. A coordinates system may be created to relate the location and orientation of the femur, tibia, boot, and slide cart to their attached trackers by identifying landmarks on these objects. Joint motions and stability test applied loads are calculated in real time from navigation system and load cell information.

The exemplary graphical user interface (GUI) illustrated in FIG. 15 was created in LabVIEW visual programming environment (National Instruments, Austin, Tex.). LabVIEW may be particularly well suited for data acquisition and creating an easy to understand graphical user interface. MATLAB (The MathWorks Inc., Natrick, Mass.) ".m" files were incorporated into the LabVIEW code to facilitate communication with the tracking system and to help perform calculations of the reference frames, knee kinematics, and knee stability data.

Figure 16:
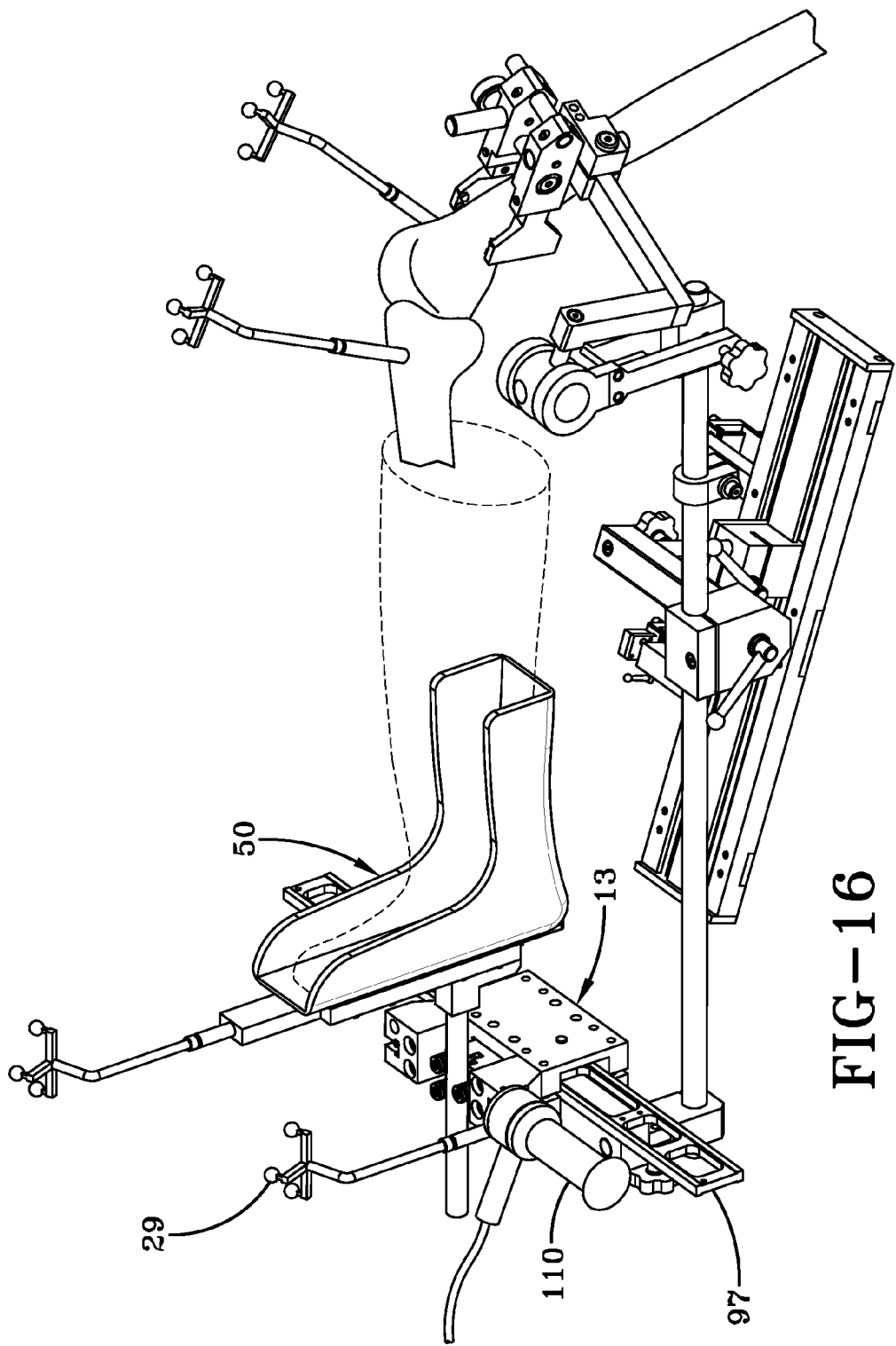
FIG. 16 shows an exemplary setup for assessing varus/valgus stability in the knee.

FIG. 16 shows an exemplary setup for assessing varus/valgus stability in the knee. Note the positions of instrumented handle 110 on cart 13 in relation to boot 50. Cart 13 may slide medial laterally on track 97. Optical trackers 29 are used to record position and orientation.

Figure 17:
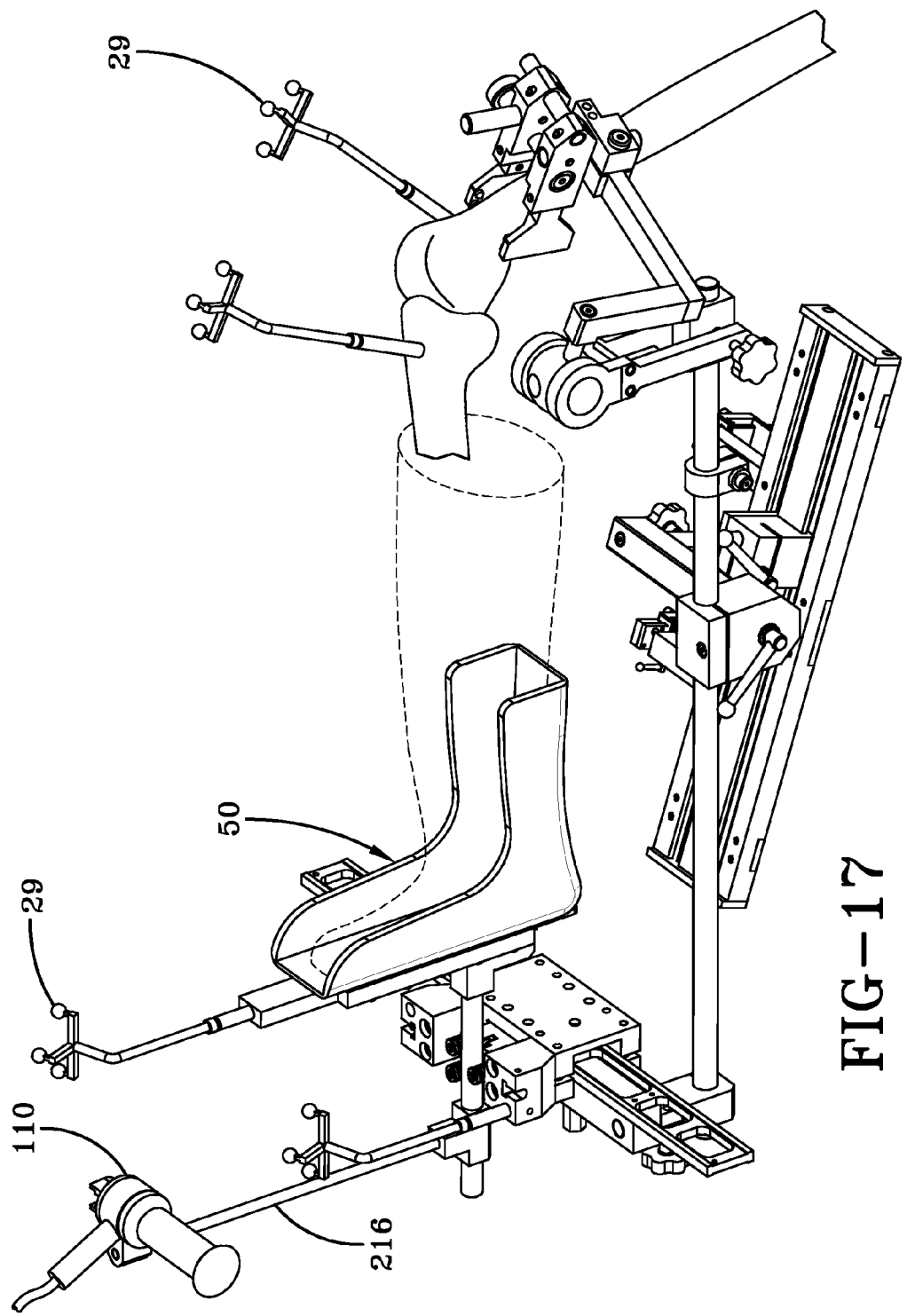
FIG. 17 shows an exemplary setup for assessing internal/external stability in the knee.

FIG. 17 shows an exemplary setup for assessing internal/external stability in the knee. Note the positions of instrumented handle 110 on lever arm 216 in relation to boot 50. Optical trackers 29 are used to record position and orientation.

Figure 18:
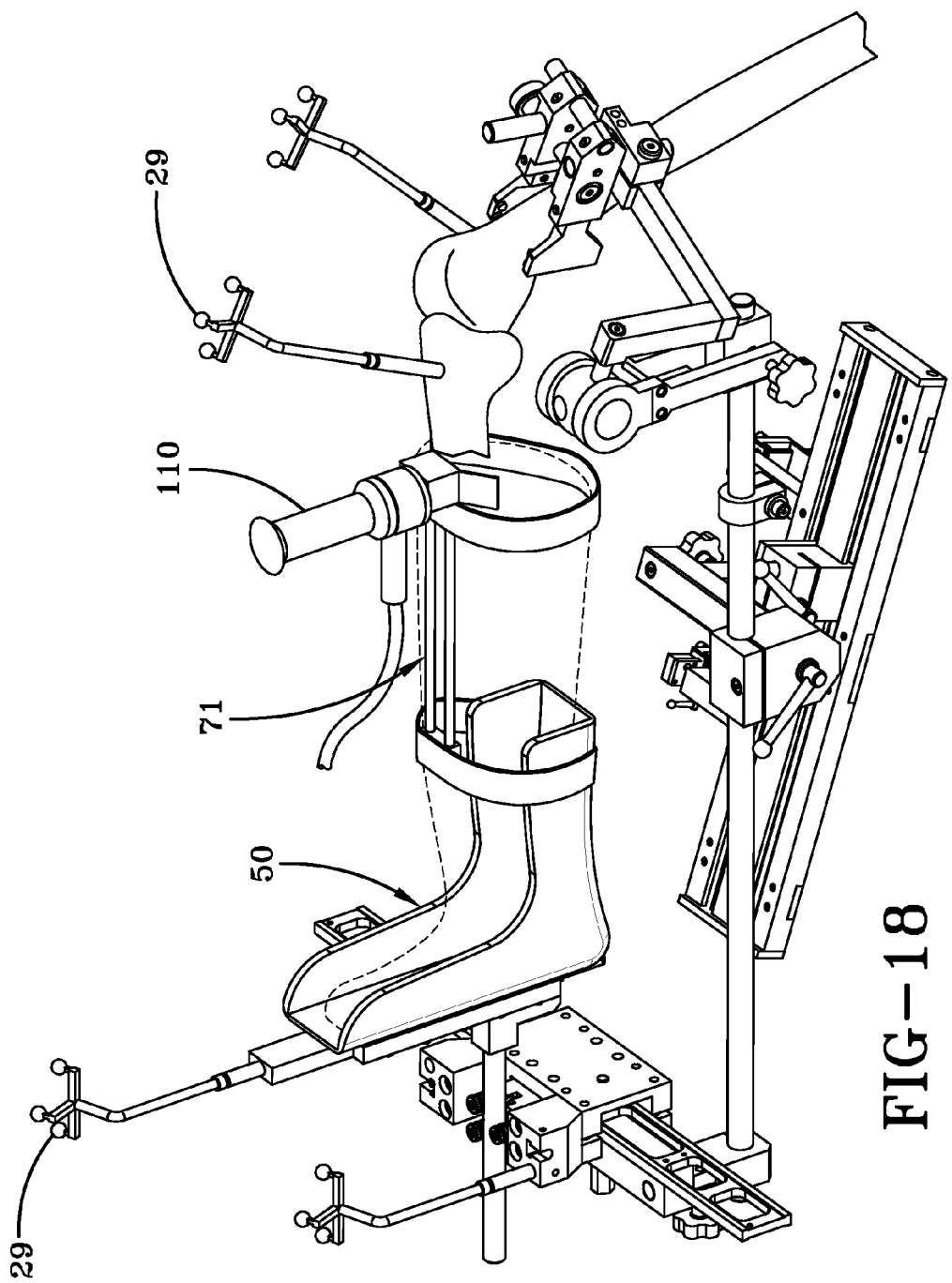
FIG. 18 shows an exemplary setup for assessing anterior/posterior stability in the knee.

FIG. 18 shows an exemplary setup for assessing anterior/posterior stability in the knee. Note the positions of instrumented handle 110 on bracket 71 in relation to boot 50. Optical trackers 29 are used to record position and orientation.

Experimental Data

The performance of an embodiment with a mechanical lower extremity, comprising a rigid metal thigh and shank links connected with a hinge to represent the knee, was tested. A 6 degree-of freedom load cell 113 (Model 2667, R.A. Denton Inc., Rochester, N.Y.) was built into the leg, with its center located 11.7 cm distal to the knee hinge.

The intra-observer and inter-observer repeatability of the device was tested in a series of experiments involving 6 observers. Each observer made 4 sets of measurements five times each on our simulated lower extremity with the "knee" at 0° and 90° of flexion: varus/valgus stability with the "knee" at 0° of varus/valgus alignment, varus/valgus stability with the "knee" at 10° of varus alignment, internal/external stability, and anterior/posterior stability. One observer repeated the entire set of measurements five additional times. In all trials, the observers applied ±60 Nm of varus/valgus moment, ±20 Nm of axial moment, and ±100 N of anterior/posterior load at 0° of knee flexion and ±45 Nm of varus/valgus moment, ±15 Nm of axial moment, and ±100 N of anterior/posterior load at 90° of knee flexion. At all loading conditions, the position of the mechanical limb was measured with the custom measurement device.

The measurement error was considered to be the difference between the moment/force calculated by the new device and the moment/force recorded by the load cell. The coefficient of determination ($R^2$) was used to determine the relationship between the moment/force calculated by the new device and the moment/force recorded by the load cell.

The results from our inter-observer and intra-observer experiments are summarized in Tables 1 and 2 below. Coefficients of determination are shown in Table 3.

TABLE 1

Inter-Observer Errors for the Stability Device

| Description of Test | Mean ± Standard Deviation |
|---|---|
| Varus/valgus, 0° varus, 0° flexion | 0.17 ± 2.50 Nm |
| Varus/valgus, 0° varus, 90° flexion | −0.20 ± 1.50 Nm |
| Varus/valgus, 10° varus, 0°, flexion | −0.08 ± 1.83 Nm |
| Varus/valgus, 10° varus, 90° flexion | −0.20 ± 1.14 Nm |
| Internal/external, 0° flexion | −0.21 ± 1.38 Nm |
| Internal/external, 90° flexion | 0.06 ± 0.97 Nm |
| Anterior/posterior, 0° flexion | 0.98 ± 3.93 N |
| Anterior/posterior, 90° flexion | −0.09 ± 3.42 N |

TABLE 2

Intra-Observer Errors for the Stability Device

| Description of Test | Mean ± Standard Deviation |
|---|---|
| Varus/valgus, 0° varus, 0° flexion | −0.29 ± 1.48 Nm |
| Varus/valgus, 0° varus, 90° flexion | −0.30 ± 1.25 Nm |
| Varus/valgus, 10° varus, 0° flexion | 0.00 ± 1.58 Nm |
| Varus/valgus, 10° varus, 90° flexion | −0.15 ± 1.24 Nm |
| Internal/external, 0° flexion | 0.04 ± 1.40 Nm |
| Internal/external, 90° flexion | 0.17 ± 0.88 Nm |
| Anterior/posterior, 0° flexion | 0.77 ± 5.43 N |
| Anterior/posterior, 90° flexion | 0.45 2.43 N |

TABLE 3

Coefficients of Determination ($R^2$)

| Description of Test | Inter-observer | Intra-observer |
|---|---|---|
| Varus/valgus, 0° varus, 0° flexion | 0.9948 | 0.9979 |
| Varus/valgus, 0° varus, 90° flexion | 0.9972 | 0.9981 |
| Varus/valgus, 10° varus, 0° flexion | 0.9971 | 0.9973 |
| Varus/valgus, 10° varus, 90° flexion | 0.9984 | 0.9975 |
| Internal/external, 0° flexion | 0.9889 | 0.9899 |
| Internal/external, 90° flexion | 0.9908 | 0.9952 |
| Anterior/posterior, 0° flexion | 0.9947 | 0.9912 |
| Anterior/posterior, 90° flexion | 0.9964 | 0.9980 |

Tested embodiments proved accurate (i.e., has low mean measurement errors) and precise (low standard deviation of the error). The maximum observed errors were 15.5 Nm for varus/valgus tests, 7.0 Nm for internal/external tests, and 25.8 N for anterior/posterior tests.

Other Embodiments

It may be to be understood that while embodiments have been described in conjunction with the detailed description thereof, the foregoing description may be intended to illustrate and not limit the scope of the invention. Other aspects, advantages, and modifications are within the scope of the following claims. For example, the above embodiments of the device are useful for total knee replacement (arthroplasty). However, the described technology of intra-operatively assessing joint laxity and stability is broadly applicable to almost any type joint replacement (e.g., hip, ankle, shoulder, elbow, etc.), or any sort of orthopaedic joint surgery in general (e.g., anterior cruciate ligament (ACL) reconstruction, MCL/LCL surgeries, PCL surgery, meniscal repair, tissue-engineering knee surgeries, knee cartilage replacement/treatment surgeries, hip resurfacing, shoulder/rotator cuff repair, etc.), elbow. With predictable modifications, the device may also be useful for many veterinary applications as well. Additionally the device may be useful for non-surgical applications, for example, in sports medicine.

What is claimed is:

1. An arrangement for assessing three-axis stability of a joint of an animal limb, the joint positioned between a proximal portion and a distal portion of the limb, the distal portion having a longitudinal axis, comprising:
a means for rigidly fixing a distal end of the proximal portion of the limb relative to the joint;
a means for receiving and holding a distal end of the distal portion;
an instrumented handle, detachably engagable upon the means for receiving and holding, for applying an amount of force to the joint to assess, depending upon where the force is applied, a stability of the joint to each of: a varus moment, a valgus moment, a rotation in an internal direction, a rotation in an external direction, a force in an anterior direction and a force in a posterior direction; and
a means for monitoring the amount of force applied by the force-applying means;
a means for monitoring, in three-dimensional space, a position and an orientation of the rigidly fixing means relative to the receiving and holding means; and
computing means for receiving data generated from the means for monitoring orientation and position and the means for monitoring applied force, calculating joint motions and applied forces and moments in real time from the received data and displaying results of the calculations.

2. The arrangement of claim 1, wherein:
the means for receiving and holding comprises:
a support, adapted for receiving and holding a distal end of the distal linear portion of the limb;
a frame, connected to the rigidly fixing means and the support, the frame being adjustable to move the joint in a selected one of an anterior and a posterior direction;
a track, coupling the support to the frame to move the joint in a direction that imparts on the joint a moment that is a selected one of a varus and a valgus moment; and
a lever arm, connected to the support and positioned to rotate the support about a selected one of an internal and an external direction of the joint.

3. The arrangement of claim 2, further comprising:
a bracket, positioned between the support and the joint and adapted for rigid attachment to the distal linear portion of the limb, the detachable engagement of the instrumented handle occurring by means of the bracket.

4. The arrangement of claim 2, wherein:
the instrumented handle comprises a load cell, operable under either tension or compression.

5. The arrangement of claim 2, wherein:
the instrumented handle detachably engages the support and the lever arm in one of two oppositely disposed orientations.

6. The arrangement of claim 2, wherein:
the instrumented handle further comprises linear bearings and a semi-flexible rod.

7. The arrangement of claim 2, further comprising:
a boot, adapted for receiving the distal linear portion of the limb as a part of the support.

8. The arrangement of claim 2, further comprising:
a lock for selectively locking the support to the track along the length thereof.

9. The arrangement of claim 2, wherein:
the means for rigidly fixing the distal end of the proximal portion is a clamp.

10. The arrangement of claim 9, wherein:
the frame allows a flexion angle in the range of about 0 to about 90 degrees between the proximal and distal linear portions of the limb.

11. The arrangement of claim 10, wherein:
the frame comprises a telescoping rod.

12. The arrangement of claim 10, wherein:
the frame further comprises a ball clamp that connects the track and the clamp.

13. The arrangement of claim 1, wherein:
the means for monitoring position and orientation comprises:
an optical tracker; and
a camera.

14. The arrangement of claim 1, wherein:
the means for monitoring position and orientation comprises an at least semi-active robot.

15. The arrangement of claim 1, wherein:
the computing means comprises:
a computer, programmed with software for receiving position and orientation data and applied force data to calculate joint motions and applied forces or moments in real time; and
a graphical user interface, associated with the computer to display the calculated joint motions and applied forces or moments.

16. The arrangement of claim 2, further comprising:
a cart, slidably engaged to the track, the detachable engagement of the instrumented handle occurring by means of the cart.

17. An arrangement for assessing three-axis stability of a joint of an animal limb, the joint positioned between a proximal portion and a distal portion of the limb, the distal portion having a longitudinal axis, comprising:
a means for rigidly fixing a distal end of the proximal portion of the limb relative to the joint;
a support, adapted to receive and hold a distal end of the distal linear portion of the limb;
a frame, connected to the rigidly fixing means and to the support, the frame arranged to adjustably move the joint in a selected one of an anterior and a posterior direction;
a track, coupling the support to the frame to impart on the joint a selected one of a varus moment and a valgus moment;
a lever arm, connected to the support and positioned to rotate the support about a selected one of an internal and an external direction of the joint;
an instrumented handle, operative upon the support, detachably engagable to apply a quantifiable amount of force in at least one of: a varus moment, a valgus moment, a rotation in an internal direction, a rotation in an external direction, a force in an anterior direction and a force in a posterior direction;
a means for monitoring the amount of force applied by the force-applying means;
an optical tracker and a camera for monitoring, in three-dimensional space, a position and an orientation of the rigidly fixing means relative to the receiving and holding means;
a computer, programmed with software for receiving position and orientation data and applied force data to calculate joint motions and applied forces/moments in real time; and
a graphical user interface, associated with the computer to display the calculated joint motions and applied forces and moments.

18. An arrangement for assessing three-axis stability of a joint of an animal limb, the joint positioned between a proximal portion of the limb and a distal portion of the limb, the distal portion having a longitudinal axis, comprising:
- a clamp, sized and adapted to rigidly fix, relative to the joint, a distal end of the proximal portion of the limb;
- a boot, sized and adapted to receive and hold a distal end of the distal portion of the limb;
- a boot peg, extending perpendicularly from a sole of the boot;
- a cart, connected to the boot by means of the boot peg;
- a track, arranged for linear sliding movement of the cart therealong to assess stability of the joint to each of a varus moment and a valgus moment;
- a frame, connected to each of the clamp and the track, the frame arranged to assess stability of the joint to each of an anterior force and a posterior force;
- a lever arm, connected to the boot and arranged to rotate the boot about the boot peg to assess stability of the joint to each of an internal rotation and an external rotation;
- an instrumented handle for applying a quantifiable amount of force, the instrumented handle used to assess:
  - stability of the joint to each of a varus moment and a valgus moment when detachably engaged to the cart;
  - stability of the joint to each of an anterior force and a posterior force when detachably engaged to a bracket positioned on the distal portion of the limb; and
  - stability of the joint to each of an internal rotation and an external rotation when detachably engaged to the lever arm;
- a means for monitoring the amount of force applied by the instrumented handle;
- an optical tracker and a camera for monitoring, in three-dimensional space, a position and an orientation of the clamp relative to the boot;
- a computer, programmed with software for receiving the position and orientation data and the applied force data to calculate joint motions and applied forces/moments in real time; and
- a graphical user interface, associated with the computer to display the calculated joint motions and applied forces and moments.

* * * * *